(12) United States Patent
Weston

(10) Patent No.: US 9,272,080 B2
(45) Date of Patent: *Mar. 1, 2016

(54) FLEXIBLE REDUCED PRESSURE TREATMENT APPLIANCE

(71) Applicant: BlueSky Medical Group Incorporated, Memphis, TN (US)

(72) Inventor: Richard Scott Weston, Encinitas, CA (US)

(73) Assignee: BlueSky Medical Group Incorporated, Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/446,688

(22) Filed: Jul. 30, 2014

(65) Prior Publication Data

US 2014/0343519 A1 Nov. 20, 2014

Related U.S. Application Data

(60) Continuation of application No. 12/719,767, filed on Mar. 8, 2010, now Pat. No. 8,795,243, which is a division of application No. 11/064,813, filed on Feb. 24, 2005, now Pat. No. 8,062,272.

(60) Provisional application No. 60/573,655, filed on May 21, 2004.

(51) Int. Cl.
*A61M 1/00* (2006.01)
*A61M 39/02* (2006.01)
(Continued)

(52) U.S. Cl.
CPC ............ *A61M 1/0088* (2013.01); *A61M 1/0031* (2013.01); *A61M 1/0001* (2013.01); *A61M 2205/075* (2013.01)

(58) Field of Classification Search
CPC ....... A61M 1/00; A61M 39/02; A61M 27/00; A61F 13/00; A61F 5/00; A61L 15/00
See application file for complete search history.

(56) References Cited

U.S. PATENT DOCUMENTS

| 774,529 | A | 11/1904 | Nieschange |
| 1,480,562 | A | 1/1924 | Mock |

(Continued)

FOREIGN PATENT DOCUMENTS

| CA | 2238413 A1 | 5/1997 |
| CA | 2471780 A1 | 3/1999 |

(Continued)

OTHER PUBLICATIONS

U.S. Appl. No. 10/599,720, filed Oct. 6, 2006, Blott et al.

(Continued)

*Primary Examiner* — Tatyana Zalukaeva
*Assistant Examiner* — Ilya Treyger
(74) *Attorney, Agent, or Firm* — Knobbe Martens Olson & Bear LLP

(57) ABSTRACT

A wound treatment appliance is provided for treating all or a portion of a wound. In some embodiments, the appliance comprises an impermeable flexible overlay that covers all or a portion of the wound for purposes of applying a reduced pressure to the covered portion of the wound. In other embodiments, the wound treatment appliance also includes a vacuum system to supply reduced pressure to the wound in the area under the flexible overlay. In yet other embodiments, the wound treatment appliance also includes wound packing means to prevent overgrowth of the wound or to encourage growth of the wound tissue into an absorbable matrix comprising the wound packing means. In still other embodiments, the appliance may include a suction drain. In other embodiments, the appliance may include a collection chamber to collect and store exudate from the wound. In yet other embodiments, a suction bulb may be used to provide a source of reduced pressure to an impermeable overlay that covers all or a portion of the wound. Finally, methods are provided for using various embodiments of the wound treatment appliance.

15 Claims, 7 Drawing Sheets

(51) Int. Cl.
 *A61M 27/00* (2006.01)
 *A61F 13/00* (2006.01)

(56) References Cited

U.S. PATENT DOCUMENTS

| | | | |
|---|---|---|---|
| 1,585,104 A | 5/1926 | Montgomery |
| 1,732,310 A | 12/1929 | Naibert |
| 1,863,534 A | 6/1932 | Odell |
| 1,936,120 A | 11/1933 | Fisk |
| 2,122,121 A | 6/1938 | Tillotson |
| 2,195,771 A | 4/1940 | Estler |
| 2,280,915 A | 4/1942 | Johnson |
| 2,367,690 A | 7/1943 | Purdy |
| 2,366,799 A | 1/1945 | Luisada |
| 2,568,933 A | 9/1951 | Robbins |
| 2,632,443 A | 3/1953 | Lesher |
| 2,682,873 A | 7/1954 | Evans et al. |
| 3,026,874 A | 11/1959 | Stevens |
| 2,927,577 A | 3/1960 | Nicolaie |
| 3,042,041 A | 7/1962 | Jascalevich |
| 3,123,074 A | 3/1964 | Turner |
| 3,217,707 A | 11/1965 | Werding |
| 3,238,937 A | 3/1966 | Stein |
| 3,286,711 A | 11/1966 | MacLeod |
| 3,315,665 A | 4/1967 | MacLeod |
| 3,367,332 A | 2/1968 | Groves |
| 3,376,868 A | 4/1968 | Mondiadis |
| 3,465,748 A | 9/1969 | Kravchenko |
| 3,486,504 A | 12/1969 | Austin, Jr. |
| 3,568,675 A | 3/1971 | Harvey |
| 3,572,340 A | 3/1971 | Lloyd et al. |
| 3,610,238 A | 10/1971 | Rich, Jr. |
| 3,712,298 A | 1/1973 | Snowdon |
| 3,794,035 A | 2/1974 | Brenner |
| 3,859,989 A | 1/1975 | Spielberg |
| 3,874,387 A | 4/1975 | Barbieri |
| 3,938,540 A | 2/1976 | Holbrook et al. |
| 3,961,625 A | 6/1976 | Dillon |
| 3,988,793 A | 11/1976 | Abitbol |
| 3,993,080 A | 11/1976 | Loseff |
| RE29,319 E | 7/1977 | Nordby et al. |
| 4,080,970 A | 3/1978 | Miller |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,256,109 A | 3/1981 | Nichols |
| 4,316,466 A | 2/1982 | Babb |
| 4,382,441 A | 5/1983 | Svedman |
| 4,444,548 A | 4/1984 | Andersen et al. |
| 4,459,139 A | 7/1984 | vonReis et al. |
| 4,465,485 A | 8/1984 | Kashmer et al. |
| 4,468,227 A | 8/1984 | Jensen |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,655,754 A | 4/1987 | Richmond et al. |
| 4,655,766 A | 4/1987 | Theeuwes et al. |
| 4,691,695 A | 9/1987 | Birk et al. |
| 4,710,165 A | 12/1987 | McNeil et al. |
| 4,738,249 A | 4/1988 | Linman |
| 4,753,231 A | 6/1988 | Lang et al. |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,820,284 A | 4/1989 | Hauri |
| 4,826,494 A | 5/1989 | Richmond et al. |
| 4,841,962 A | 6/1989 | Berg et al. |
| 4,847,083 A | 7/1989 | Clark |
| 4,921,488 A | 5/1990 | Maitz et al. |
| 4,936,834 A | 6/1990 | Beck et al. |
| 4,950,483 A | 8/1990 | Ksander |
| 4,969,880 A | 11/1990 | Zamierowski |
| 4,972,829 A | 11/1990 | Knerr |
| 4,979,944 A | 12/1990 | Luzsicza |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,228,431 A | 7/1993 | Giarretto |
| 5,234,419 A | 8/1993 | Bryant et al. |
| 5,261,893 A | 11/1993 | Zamierowski |
| 5,264,218 A | 11/1993 | Rogozinski |
| 5,266,928 A | 11/1993 | Johnson |
| 5,279,608 A | 1/1994 | Cherif Cheikh |
| 5,328,614 A | 7/1994 | Matsumura |
| 5,358,494 A | 10/1994 | Svedman |
| 5,362,543 A | 11/1994 | Nickerson |
| 5,380,280 A | 1/1995 | Peterson |
| 5,437,651 A | 8/1995 | Todd et al. |
| 5,445,604 A | 8/1995 | Lang |
| 5,462,514 A | 10/1995 | Harris |
| 5,489,280 A | 2/1996 | Russell |
| 5,498,338 A | 3/1996 | Kruger et al. |
| 5,527,293 A | 6/1996 | Zamierowski |
| 5,549,584 A | 8/1996 | Gross |
| 5,563,233 A | 10/1996 | Reich et al. |
| 5,618,556 A | 4/1997 | Johns et al. |
| 5,636,643 A | 6/1997 | Argenta |
| 5,643,189 A | 7/1997 | Masini |
| 5,645,081 A | 7/1997 | Argenta |
| 5,688,225 A | 11/1997 | Walker |
| 5,701,917 A | 12/1997 | Khouri |
| 5,716,411 A | 2/1998 | Orgill et al. |
| 5,759,570 A | 6/1998 | Arnold |
| 5,785,688 A | 7/1998 | Joshi et al. |
| 5,827,246 A | 10/1998 | Bowen |
| 5,830,496 A | 11/1998 | Freeman |
| 5,833,646 A | 11/1998 | Masini |
| 5,857,502 A | 1/1999 | Buchalter |
| 5,868,933 A | 2/1999 | Patrick et al. |
| 5,885,237 A | 3/1999 | Kadash |
| 5,893,368 A | 4/1999 | Sugerman |
| 5,938,626 A | 8/1999 | Sugerman |
| 5,964,723 A | 10/1999 | Augustine |
| 5,970,266 A | 10/1999 | Takato |
| 6,045,541 A | 4/2000 | Matsumoto et al. |
| 6,071,267 A | 6/2000 | Zamierowski |
| 6,110,197 A | 8/2000 | Augustine et al. |
| 6,113,548 A | 9/2000 | deBoisblanc et al. |
| 6,135,116 A | 10/2000 | Vogel et al. |
| D434,150 S | 11/2000 | Tumey |
| 6,142,982 A | 11/2000 | Hunt |
| 6,168,800 B1 | 1/2001 | Dobos et al. |
| 6,176,307 B1 | 1/2001 | Danos et al. |
| 6,200,596 B1 | 3/2001 | Schwartzmiller et al. |
| 6,225,523 B1 | 5/2001 | Masini |
| 6,254,567 B1 | 7/2001 | Treu et al. |
| 6,255,552 B1 | 7/2001 | Cummings et al. |
| 6,287,521 B1 | 9/2001 | Quay et al. |
| 6,345,623 B1 | 2/2002 | Heaton et al. |
| 6,371,976 B1 | 4/2002 | Vrzalik |
| 6,398,767 B1 | 6/2002 | Fleischmann |
| 6,402,724 B1 | 6/2002 | Smith et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,509,391 B2 | 1/2003 | Gothjaelpsen et al. |
| 6,553,998 B2 | 4/2003 | Heaton et al. |
| 6,566,833 B2 | 5/2003 | Bartlett |

(56) References Cited

U.S. PATENT DOCUMENTS

| | | |
|---|---|---|
| 6,571,825 B2 | 6/2003 | Stacy |
| 6,595,949 B1 | 7/2003 | Shapiro |
| 6,599,262 B1 | 7/2003 | Masini |
| 6,648,862 B2 | 11/2003 | Watson |
| 6,673,028 B1 | 1/2004 | Argenta et al. |
| 6,676,610 B2 | 1/2004 | Morton et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,904,631 B2 | 6/2005 | Vrzalik et al. |
| 6,936,037 B2 | 8/2005 | Bubb et al. |
| 6,951,553 B2 | 10/2005 | Bubb et al. |
| 6,977,323 B1 | 12/2005 | Swenson |
| 6,979,324 B2 | 12/2005 | Bybordi et al. |
| 6,988,423 B2 | 1/2006 | Bolam et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| 7,144,390 B1 | 12/2006 | Hannigan et al. |
| 7,195,624 B2 | 3/2007 | Lockwood |
| 7,216,651 B2 | 5/2007 | Argenta et al. |
| 7,279,612 B1 | 10/2007 | Heaton et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,470,830 B2 | 12/2008 | Sigurjonsson et al. |
| 7,494,482 B2 | 2/2009 | Orgill et al. |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,699,830 B2 | 4/2010 | Martin |
| 7,708,724 B2 | 5/2010 | Weston |
| 7,723,560 B2 | 5/2010 | Lockwood et al. |
| 7,731,702 B2 | 6/2010 | Bybordi |
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,799,004 B2 | 9/2010 | Tumey |
| 7,815,616 B2 | 10/2010 | Boehringer et al. |
| 7,828,782 B2 | 11/2010 | Suzuki |
| 7,846,141 B2 | 12/2010 | Weston |
| 7,883,494 B2 | 2/2011 | Martin |
| 7,896,856 B2 | 3/2011 | Petrosenko et al. |
| 7,909,805 B2 | 3/2011 | Weston |
| 7,927,318 B2 | 4/2011 | Risk, Jr. et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,012,169 B2 | 9/2011 | Joshi |
| 8,034,037 B2 | 10/2011 | Adams et al. |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,162,909 B2 | 4/2012 | Blott et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,235,955 B2 | 8/2012 | Blott et al. |
| 8,241,261 B2 | 8/2012 | Randolph et al. |
| 8,257,327 B2 | 9/2012 | Blott et al. |
| 8,282,611 B2 | 10/2012 | Weston |
| 8,303,552 B2 | 11/2012 | Weston |
| 8,338,402 B2 | 12/2012 | Fry et al. |
| 8,348,910 B2 | 1/2013 | Blott et al. |
| 8,398,614 B2 | 3/2013 | Blott et al. |
| 8,444,612 B2 | 5/2013 | Patel et al. |
| 8,449,509 B2 | 5/2013 | Weston |
| 8,460,255 B2 | 6/2013 | Joshi et al. |
| 8,535,296 B2 | 9/2013 | Blott et al. |
| 8,540,699 B2 | 9/2013 | Miller et al. |
| 8,569,566 B2 | 10/2013 | Blott et al. |
| 8,628,505 B2 | 1/2014 | Weston |
| 8,641,691 B2 | 2/2014 | Fink et al. |
| 8,663,198 B2 | 3/2014 | Buan et al. |
| 8,708,998 B2 | 4/2014 | Weston et al. |
| 8,715,256 B2 | 5/2014 | Greener |
| 8,764,732 B2 | 7/2014 | Hartwell |
| 8,784,393 B2 | 7/2014 | Weston et al. |
| 8,795,243 B2 | 8/2014 | Weston |
| 8,808,274 B2 | 8/2014 | Hartwell |
| 8,852,149 B2 | 10/2014 | Weston et al. |
| 2001/0034499 A1 | 10/2001 | Sessions et al. |
| 2002/0068913 A1 | 6/2002 | Fleischmann |
| 2002/0115952 A1 | 8/2002 | Johnson |
| 2002/0143286 A1 | 10/2002 | Tumey |
| 2002/0161346 A1 | 10/2002 | Lockwood et al. |
| 2002/0183702 A1 | 12/2002 | Henley et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0125646 A1 | 7/2003 | Whitlock |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0039391 A1 | 2/2004 | Argenta et al. |
| 2004/0064132 A1 | 4/2004 | Boehringer et al. |
| 2004/0122434 A1 | 6/2004 | Argenta et al. |
| 2004/0241214 A1 | 12/2004 | Kirkwood et al. |
| 2006/0029650 A1 | 2/2006 | Coffey |
| 2007/0038172 A1 | 2/2007 | Zamierowski |
| 2007/0185463 A1 | 8/2007 | Mulligan |
| 2007/0239139 A1 | 10/2007 | Weston et al. |
| 2008/0132819 A1 | 6/2008 | Radl et al. |
| 2008/0167593 A1 | 7/2008 | Fleischmann |
| 2008/0188820 A1 | 8/2008 | Joshi |
| 2008/0223378 A1 | 9/2008 | Henderson et al. |
| 2009/0054855 A1 | 2/2009 | Blott et al. |

(56) References Cited

U.S. PATENT DOCUMENTS

| | | |
|---|---|---|
| 2009/0124988 A1 | 5/2009 | Coulthard |
| 2009/0131888 A1 | 5/2009 | Joshi |
| 2009/0137973 A1 | 5/2009 | Karpowicz et al. |
| 2009/0204085 A1 | 8/2009 | Biggie et al. |
| 2009/0216170 A1 | 8/2009 | Robinson et al. |
| 2009/0221977 A1 | 9/2009 | Blott et al. |
| 2009/0227969 A1 | 9/2009 | Jaeb et al. |
| 2009/0234309 A1 | 9/2009 | Vitaris et al. |
| 2009/0240185 A1 | 9/2009 | Jaeb et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0306580 A1 | 12/2009 | Blott et al. |
| 2009/0312723 A1 | 12/2009 | Blott et al. |
| 2010/0036367 A1 | 2/2010 | Krohn |
| 2010/0069858 A1 | 3/2010 | Olson |
| 2010/0069863 A1 | 3/2010 | Olson |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0249733 A9 | 9/2010 | Blott et al. |
| 2010/0286635 A1 | 11/2010 | Watson, Jr. |
| 2010/0305490 A1 | 12/2010 | Coulthard et al. |
| 2010/0324510 A1 | 12/2010 | Andresen et al. |
| 2011/0004172 A1 | 1/2011 | Eckstein et al. |
| 2011/0009835 A1 | 1/2011 | Blott et al. |
| 2011/0034892 A1 | 2/2011 | Buan |
| 2011/0054422 A1 | 3/2011 | Locke et al. |
| 2011/0054423 A1 | 3/2011 | Blott et al. |
| 2011/0092927 A1 | 4/2011 | Wilkes et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0230849 A1 | 9/2011 | Coulthard et al. |
| 2011/0282309 A1 | 11/2011 | Adie et al. |
| 2012/0041399 A1 | 2/2012 | Blott et al. |
| 2012/0053538 A1 | 3/2012 | Blott et al. |
| 2012/0136325 A1 | 5/2012 | Allen et al. |
| 2012/0209224 A1 | 8/2012 | Weston |
| 2013/0110058 A1 | 5/2013 | Adie et al. |
| 2014/0012214 A1 | 1/2014 | Miller |

FOREIGN PATENT DOCUMENTS

| | | |
|---|---|---|
| CA | 2432293 A1 | 2/2003 |
| CA | 2490027 A1 | 12/2003 |
| DE | 3935818 | 10/1990 |
| DE | 4012232 A1 | 10/1991 |
| DE | 19844355 | 4/2000 |
| DE | 202005019670 U1 | 12/2005 |
| EP | 0020662 B1 | 7/1984 |
| EP | 0355186 A | 2/1990 |
| EP | 0782421 | 7/1999 |
| EP | 1121163 | 4/2000 |
| EP | 1088 569 A | 4/2001 |
| EP | 0708620 | 5/2003 |
| EP | 1440667 | 3/2006 |
| EP | 1284777 | 4/2006 |
| EP | 1171065 | 3/2007 |
| EP | 1476217 | 3/2008 |
| EP | 2 098 257 | 9/2009 |
| FR | 1163907 | 5/1958 |
| GB | 114754 | 4/1918 |
| GB | 641061 | 8/1950 |
| GB | 1224009 A | 3/1971 |
| GB | 1549756 A | 8/1979 |
| GB | 2195255 A | 4/1988 |
| GB | 2378392 A | 2/2003 |
| JP | 2003-165843 | 6/2003 |
| RU | 240188 | 3/1969 |
| SU | 1251912 A1 | 8/1986 |
| WO | WO 84/01904 | 5/1984 |
| WO | WO 87/04626 | 8/1987 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 99/01173 | 1/1999 |
| WO | WO 00/07653 | 2/2000 |
| WO | WO 00/50143 | 8/2000 |
| WO | WO 00/59424 | 10/2000 |
| WO | WO 01/19430 | 3/2001 |
| WO | WO 01/34223 | 5/2001 |
| WO | WO 01/85248 | 11/2001 |
| WO | WO 01/93793 | 12/2001 |
| WO | WO 02/083046 | 10/2002 |
| WO | WO 02/092783 | 11/2002 |
| WO | WO 03/092620 | 11/2003 |
| WO | WO 2004/024300 | 3/2004 |
| WO | WO 2004/037334 | 5/2004 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |

OTHER PUBLICATIONS

U.S. Appl. No. 12/192,000, filed Apr. 14, 2008, Hartwell.
U.S. Appl. No. 12/192,000, filed Aug. 14, 2008, Hartwell et al.
International Search Report of International Application No. PCT/GB00/04278 consisting of 2 pages, Feb. 22, 2001.
International Search Report of International Application No. PCT/NL2004/000565 consisting of 5 pages, Jul. 29, 2005.
International Search Report of International Application No. PCT/US2007/011278 consisting of 6 pages, May 11, 2006.
International Search Report of PCT/US2007/011321, International Filing Date May 10, 2007.
International, Written Opinion of the International Searching Authority of PCT International Search Report of PCT/US2007/011321, International Filing Date May 10, 2007.
International Search Report of International Application No. PCT/GB00/01566 consisting of 2 pages, Sep. 25, 2000.
International Preliminary Report, International Application No. PCT/US2005/17225, dated Jul. 31, 2006, in 6 pages.
International Search Report, International Application No. PCT/US2005/17225, dated Oct. 4, 2005, in 1 page.
Achterberg et al., "Hydroactive dressings and serum proteins: an in vitro study," Journal of Wound Care, vol. 5, No. 2, Feb. 1996 (pp. 79-82).
Argenta, Louis C., et al., "Vacuum-Assisted Closure, A New Method for Wound Control and Treatment; Clinical Experience", Ann Plas Surg 1997;38,563-577 (Dec. 10, 1996).
Aubrey, D.A., et al., Treatment of the Perineal Wound after Proctectomy by Intermittent Irrigation, *Arch. Surg.*, Oct. 1984, 119, 1141-1144.
Bagautdinov, N. A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.
Biblehimer, Helen L., "Dealing With a Wound that Drains 1.5 Liters a Day," RN, Aug. 1986, pp. 21-23, USA.
Bier, A., *Hyperemia as a Therapeutic Agent*, Ed. Dr. Gustavus M. Blech, A. Robertson & Co., Chicago 1905.
Brubacher, Lynda L., "To Heal a Draining Wound", RN, Mar. 1982, pp. 30-35, USA.
Bucalo et al. "Inhibition of Cell Proliferation by Chronic Wound Fluid." Wound Repair and Regeneration. Miami, 1993. pp. 181-186.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum mastectomy for breast cancer—a prospective randomized clinical trial", Research Article (Jan. 27, 2005), 1-5.

(56) References Cited

OTHER PUBLICATIONS

Costunchenok, B.M., et al., Effect of Vacuum on Surgical Purulent Wounds, *Vestnik Chirurgia 1986*, Sep. 18-20 (in Russian with English translation).

Davydov et al. "Pathogenic Mechanism of the Effect of Vacuum Therapy on the Course of the Wound Process" pp. 42-47 (Dec. 1990).

Davydov, Y.A., et al., Vacuum Therapy in the Treatment of Purulent Lactational Mastitis, Vestnik Chirurgia, Grexova 1986, September Edition, 66-70 (in Russian with English translation).

Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.

Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii BlueSky Publishing, La Costa, California (2004) 11-14.

De Lange, M.Y., et al., "Vacuum-Assisted Closure: Indications and Clinical Experience", Eur J Plast Surg (2000) 2;178-182 (Feb. 9, 2000).

Dilmaghani et al., "A Method for Closed Irrigation and Suction Therapy in Deep Wound Infections," Journal of Bone and Joint Surgery, 1969, vol. 51-A, No. 2, pp. 323-342.

Fleischmann, "Vacuum sealing: indication, technique, and results," *European Journal of Orthopaedic Surgery & Traumatology*, vol. 5(1), 1995, pp. 37-40.

Fleischmann, W. Wund Forum Spezial, "Vakuumversiegelung zur Behandlung von Problemwunden" (with English translation: Vacuum Sealing for Treatment of Problematical Wounds). *IHW '94*, 6 pages.

Garcia-Rinaldi, R., et al., Improving the Efficiency of Wound Drainage Catheters, *Amer. Journ. of Surg.*, Sep. 1975, 130, 372-373.

Hartz, R.S., et al., Healing of the Perineal Wound, *Arch. Surg.*, Apr. 1980, 115, 471-474.

Health Technology, Literature R., "Vacuum Assisted Closure Therapy for Wound Care", Health Technology Literature Review (Dec. 2004), 3-59.

Jeter, Katherine F. ET, Managing Draining Wounds and Fistulae: New and Established Methods, Chronic Wound Care, Chapter 27, pp. 240-246. 1990.

Johnson, F.E., An Improved Technique for Skin Graft Placement using a Suction Drain, *Surgery, Gynecology & Obstetrics*, Dec. 1984 159(6), 584-585.

KCI, Inc., If It's Not V.A.C. Therapy, It's Not Negative Pressure Wound Therapy, *KCI Brochure*, Jan. 2005, 1-5.

Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.

Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.

Kremlin Papers, A Collection of Published Studies Complementing the Research and Innovation of Wound Care, from *Vestnik Khirurgii, BlueSky Publishing, A Div. of BlueSky Medical Group Inc.*, 2004. 17 pages.

Landes, R.R. and I. Melnick, An Improved Suction Device for Draining Wounds, *Arch. Surg.*, May 1972, 104, p. 707.

Linden van der, Willem, Randomized Trial of Drainage After Cholecystectomy, Modern Operative Techniques, Voluje 141, Feb. 1981, pp. 289-294.

McFarlane, R. M., "The Use of Continuous Suction Under Skin Flaps", F.R.C.S.(c), vol. 1, pp. 77-86 (1958).

McLaughlan, James, Sterile Microenvironment for Postoperative Wound Care, The Lancet, pp. 503-504, Sep. 2, 1978.

Meyer, W. & Schmieden, V., *Bier's Hyperemic Treatment, W B. Saunders Company* 1908.

Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).

Nakayama, Y., et al., "A New Method for the Dressing of Free Skin Grafts", Plastic and Reconstructive Surgery, Dec. 1990 pp. 1216-1219, UK.

Ramirez, O.M., et al., Optimal Wound Healing under Op-Site Dressing, Ideas and Innovations, 73(3), pp. 474-475.

Ranson, John H. M.D., Safer Intraperitoneal Sump Drainage, Surgery Gynnecology and Obstetrics, pp. 841-842, 1973 vol. 137.

Sames, C.P., Sealing of Wounds with Vacuum Drainage, *Br. Med. Journ.*, Nov. 5, 1977, p. 1223, *Correspondence*.

Solovev et al., "The Method of Treatment of Immature External Fistulas in the Upper Gastrointestinal Tract," USSR Ministry of Health, S.M. Kirov Gorky State Medical Institute, 1987. (with English translation).

Solovev, V.A. "Treatment and Prevention of Suture Failures after Gastric Resection" (Dissertation Abstract) (S.M. Kirov Gorky State Medical Institute, Gorky USSR 1988).

Stewart, Joanne, "Next generation products for wound management," http://www.worldwidewounds.com/2003/april/Stewart/Next-Generation-Products.html, Nov. 2002.

Svedman, "Irrigation Treatment of Leg Ulcers," The Lancet, Sep. 3, 1983, pp. 532-534.

Svedman, P., A Dressing Allowing Continuous Treatment of a Biosurface; *IRCS Med. Science: Biomed. Tech.; Clinic. Med.; Surg. and Transplantation*, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Svedman, P., Irrigation Treatment in Split-Thickness Skin Grafting of Intractable Leg Ulcers, Scand J. Plast. Reconst. Surg., 1985, 19, pp. 211-213.

Swift, et al, Quorum Sensing in Aeromonas hydrophila and Aeromonas salmoncida: Identification of LuxRI Homologs AhyRI and AsaRI and Their Cognate N-Acylhomoserine Lactone Signal Molecules, J. Bacteriol., 1997,179(17):5271-5281.

Teder and Svedman et al., "Continuous Wound Irrigation in the Pig," Investigative Surgery, 1990, vol. 3, pp. 399-407.

Tribble, David E. M.D., An Improved Sump Drain-Irrigation Device of Simple Construction, Archives of Surgery New York, pp. 511-513, 1972 vol. 105.

Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.

Venturi, Mark L., "Mechanisms and Clinical Applications of the Vacuum-Assisted Closure (VAC) Device", Am J Clin Dermatol (2005) 693, 185-194; Review Article (2005), 185-194.

Vijanto, J. and J. Raekallio, Local Hyperalimentation of Open Wounds, *Br. J. Surg.*, 1976, 63, 427-430.

Webb, New Techniques in Wound Management: Vacuum-Assisted Wound Closure, Journal of the American Academy of Orthopaedic Surgeons, v. 10, No. 5, pp. 303-311, Sep. 2002.

Webster's Revised Unabridged Dictionary, published 1913 by C. & G. Merriam Co., definition of Flapper Valve, downloaded from Free Online Dictionary.

Westaby, S., et al., "A Wound Irrigation Device", The Lancet, Sep. 2, 1978, pp. 503-504.

Wooding-Scott, Margaret, et.al, "No Wound is Too Big for Resourceful Nurses," RN, Dec. 1988, pp. 22-25, USA.

Written Opinion of the International Search Report of PCT/US2007/011278 consisting of 7 pages, Dec. 11, 2007.

Wu, W.S., et al. Vacuum therapy as an intermediate phase in wound closure: a clinical experience, Eur J Past Surg (2000) 23: 174-177.

U.S. Appl. No. 12/260,962, filed Oct. 29, 2009, Weston.

European Exam Report, re EP Application No. EP 11 154 569.5, dated Nov. 13, 2014.

International Standard ISO 10079-1, First Edition, May 15, 1991, 2 pages.

International Written Opinion, International Application No. PCT/US2005/17225, dated Oct. 4, 2005, in 4 pages.

"General Characteristics of Wound Healing and Russian Classificaiton of Wound Healing Process,".

(56) References Cited

OTHER PUBLICATIONS

3M Health Care, Controlling the Risk of Surgical Site Infections after Cardiovascular Procedures: The Importance of Providing a Sterile Surface, *Brochure*, St. Paul, MN and London, Ontario, Canada, 1997, 8 pages.
A Sensational Medical discovery, *Brit. Journ. Nurs.*, Jul. 15, 1911, 42.
Agarwala, S., et al., Use of Mini-Vacuum Drains in Small Surgical Wounds, *Plastic and Reconstructive Surgery*, Apr. 1998, 101(5), 1421-1422 (Correspondence).
Agrama, H.M., Functional Longevity of Intraperiotoneal Drains, *Amer. Journ. of Surg.*, Sep. 1976, 132, 418-421.
Alexander, J. Wesley, "Prevention of Wound Infections," The American Journal of Surgery, Jul. 1976, pp. 59-63, vol. 132, USA.
Alper, J.C., et al., An Effective Dressing for a Large, Draining Abdominal wound, *RN*, Dec. 1988, 24-25.
Alper, J.C., et al., Moist Wound Healing under a Vapor Permeable Membrane, *Journ. of Amer. Acad. of Derm.*, Mar. 1983, 8(3), 347-353.
Alper, Joseph, C., "Recent Advances in Moist Wound Healing," Southern Medical Journal, Nov. 1986, pp. 1398-1404, vol. 79, No. 11 USA.
Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.
Article Excerpt, *Lancet*, Jun. 14, 1952 1175-1176.
Article Excerpt: Part III. Resolving Selected Clinical Dilemmas, 17-20.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, *PubMed, Abs.* Downloaded from Internet, Apr. 24, 2006, 1 page.
Assessing the Patient with a Fistula or Draining Wounds, *Nursing*, Jun. 1980, 49-51.
Avocat, C. et al., Nouvelle Presentation de Materiel Pour Drainage de Redon et Jost, *La Nouvelle Press Medicale*, Jun. 26, 1976, 5(6), 1644-1645 (in French).
Ayoub, M.H. and G. C. Bennet, A Study of Cutaneous and Intracompartmental Limb Pressures Associated with the Combined Use of Tourniquets and Plaster Casts, Abs., *Proc. and Reports of Univ. Colleges, Councils, Assoc., and Societies*, 68-8:3, May 1986, 497.
Bagautdinov, "Variant of External Vacuum Aspiration in the Treatment of Purulent Diseases of Soft Tissues," Current Problems in Modern Clinical Surgery, 1986, 4 pages.
Baldwin, J.F., Ed., The Columbus Medical Journal, Columbus, Ohio, 1887, V., 561.
Barbul, A., et al., Eds., Clinical and Experimental Approaches to Dermal and Epidermal Repair, Normal and Chronic Wounds, Progress in Clin. and Biol. Res., vol. 365, *Proc. of the 3rd Intnl. Symp. on Tissue Repair*, Miami, FL, Jan. 10-14, 1990, Abs.
Bar-El, Y. et al., Potentially dangerous Negative Intrapleural pressures Generated by Ordinary Pleural Drainage Systems, *Chest*, Feb. 2001, 119(2), 511-514.
Barker, D.E., et al., Vacuum Pack Technique of Temporary Abdominal Closure: A 7-Year Experience with 112 Patients, *Journ. of Trauma: Injury and Critical Care*, Feb. 2000, 4892), 201-207.
Bascom, J., Pilonidal Sinus, *Current Therapy in Colon and Rectal Surgery*, 1990, 1-8.
Benjamin, P.J., Faeculent Peritonitis: A Complication of Vacuum Drainage: *Br. J. Surg.*, 1980, 67, 453-454.
Berman and Fabiano, Closed Suction Drainage, *Orthopedics*, Mar. 1990, 13(3), 310-314.
Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.
Besst, J.A., Wound Healing-Intraoperative Factors, *Nursing Clinics of North America*, Dec. 1979, 14(4), 701-712.

Betancourt, Sergio, "A Method of Collecting the Effluent from Complicated Fistual of the Small Intestine," Dept. of Surgery, Allegheny General Hospital, Pittsburgh, p. 375, USA.
Birdsell, D.C., et al., The Theoretically Ideal Donor Site Dressing; Annals of Plastic Surgery, vol. 2, Jun. 1979; Gadgetry, Div. of Plastic Surgery, Foothills, Hospital, Calgary, Canada, 535-537.
Bischoff, et al., Vacuum-Sealing Fixation of Mesh Grafts, *Euro. Journ. Plast. Surg.*, Jul. 2003, 26(4), 189-190, Abs, Downloaded from internet Apr. 6, 2006.
Bonnema, J., et al., A Prospective Randomized Trial of High Versus Low Vacuum Drainage after Axillary Dissection for Breast Cancer, *Amer. Journ. Surg.*, Feb. 1997, 173, 76-79.
Boretos, John W., "Cellular Polymers for Medical Use: The Vital Role of Porosity and Permeability," Cellular Polymers, 1984, vol. 3, pp. 345-358.
Britton, B.J., et al., A Comparison Between Disposable and Non-Disposable Suction Drainage Units: A Report of a Controlled Trial, *Br. J. Surg.* 1979, 66, 279-280.
Broader, J.H., et al., Management of the Pelvic Space after Proctectomy, *Br. J. Surg.*, 1974, 62, 94-97.
Brummelkamp, W.H., et al, "High-vacuum drainage and primary perineal wound closure in abdominoperineal excision of the rectum", The Netherlands Journal of Surgery, 1991 pp. 236-238, Netherlands.
Bruno, P., The Nature of Wound Healing: Implications for Nursing Practice, *Nursing Clinics of North American*, Dec. 1979, 14(4), 667-682.
Burdette-Taylor, S.R., Use of the Versatile One (V1) for Closed Suction Drainage to Stimulate Closure in Chronic Wounds in Home Care, Case Study Presentation, 2003, 2 pgs.
Bush, G.K., What is a Counter Irritant? Name Any That You Know and the Method of their Application, *Brit. Journ. Nurs.*, Oct. 1927, 232.
Calhoun, P. and K. Kenney, Pouching Management of Patients with Open abdomen, Eviscerations and Bowel Fistulas, Case Studies, *Univ. of Miami/Jackson Memorial Medical Center*, 1 page.
Candiani, P., et al., Repair of a Recurrent Urethrovaginal Fistula with an Island Bulbocavernous Musculocutaneous Flap, *Plastic and Reconstructive Surgery*, Dec. 1993, 1393-1394.
Carroll, P.L., The Principles of Vacuum and its Use in the Hospital Environment, 2nd Ed., 1986, 30p.
Chardak et al., "Experimental Studies on Synthetic Substitutes for Skin and Their Use in the Treatment of Burns," Annals of Surgery, 1962, vol. 155, No. 1, pp. 127-139.
Chart: Influence of Wound Closure on Healing of Perineal Wound after Abdominoperineal Resection or Total Proctocolectomy, excerpt faxed Jan. 23, 2006, 1 page.
Chua Patel, C.T., et al., Vacuum-Assisted Closure, *AJN*, Dec. 2000, 100(12), 45-49.
Cobb, J.P., Why Use Drains?, *Br. J. Bone Joint Surg.*, Nov. 1990, 72-B(6), 993-995.
Cooper, D.M., Optimizing Wound Healing, *Nursing Clinics of North America*, Mar. 1990, 25(1), 163-179.
Cooper, D.M., Postsurgical Nursing Intervention as an Adjunct to Wound Healing, *Nursing Clinics of North America*, Dec. 1979, 14(4), 713-726.
Cooper, S.M. and E. Young, Topical Negative Pressure, *Commentary, International Journal of Dermatology* 2000, 39, 892-898.
Cotton, P.B., et al., Early Endoscopy of Oesophagus, Stomach, and Duodenal Bulb in patients with Haematemesis and Melaena, *Br. Med. Journ.*, Jun. 1973, 2, 505-509.
Crisp, W.J. and A. Gunn, Granuflex Dressings for Closed Surgical Wounds Combined with Suction Drainage, *Annals of the Royal College of Surgeons of England*, 1990, 72, p. 76.
Cucuroos Y.C., Vacuum Drainage of Post Operative Wounds, *Kiev Army Hospital Dept. of Hospital Surgery, Kiev medical University*, 64-65 (in Russian with English translation).
Curtin, L.L., Wound Management: care and Cost—an Overview, *Nursing Management*, Feb. 1984, 15(_), 22-25.
Davis, J.C. and T.K. Hunt, Eds., Problem Wounds: The Role of Oxygen, Chap. 1, Infection and Oxygen, 1988,1-15.
Davydov et al. "Pathogenic Mechanism of the Effect of Vacuum Therapy on the Course of the Wound Process" Dec. 1986.

(56) References Cited

OTHER PUBLICATIONS

Davydov, Y.A., et al. Justifying the Usage of Force Early Secondary Sutures in treatment of Purulent Wounds by the Vacuum Therapy, Vestnik Chirurgia 1990, Mar. Edition, 126-129 (in Russian with English translation).

Davydov, Y.A., et al., Concept of Clinico-Biological Management of Wound Process in Treatment of Purulent Wounds with the Help of Vacuum Therapy, Vestnik Chirurgia 1991, February Editions 132-135 (in Russian with English translation).

Davydov, Y.A., et al., The Bacteriological & Cytological Assessment of Vacuum Therapy of Purulent Wounds, Vestnik Chirurgia 1988, October Edition 48-52 (in Russian with English translation), 1987.

Doillon, C.J., et al., Collagen-Based Wound Dressings: Control of the Pore Structure and Morphology, Journal of Biomedical Materials Research, Sep. 13, 2004, 20(8), 1219-1228 Abs. Downloaded from Internet http://www3.interscience.wiley.com, Apr. 28, 2006.

Domkowski, P.W., et al., Evaluation of Vacuum-Assisted Closure in the Treatment of Poststernotomy Mediastinitis, *Journ. of Thorac. and Cardiovascular Surg.*, Aug. 2003, 126(2), 386-390.

Doss, Mirko. et al., Vacuum-Assisted Suction Drainage Versus Conventional Treatment in the Management of Poststernotomy Osteomyelitis, *Euro. Journ. Cardio-Thoracic. Surg. 22* ((2002) 934-938.

Draper, J., Make the Dressing Fit the Wound, *Nursing Times*, Oct. 9, 1985, 32-35.

Dunbar, J.M., State What You Have Learned Recently on the Up-to-Date Care of Wounds, *Brit. Journ. Nurs.*, Dec. 1941, 200.

Dunlop, M.G, et al. Vacuum Drainage of Groin Wounds after Vascular Surgery: A Controled Trial, Br. J. Surg., May 1990, 77, 562-563.

Eaglstein, W.H., et al., Wound Dressings: Current and Future, *Clin. and Exper. Approaches to Dermal and Epidermal Repair: Normal and Chronic Wounds*, 1991, 257-265.

ECRI, Target Report, Negative Pressure Wound Therapy for Chronic Wounds, Jan. 24, 2006, 1-7, Downloaded from internet, http://www.target.ecri.org/summary/detail.aspx?dox_id=1155.

Eisenbud, D.E., Modern Wound Management, *Anadem Publishing*, Chap. 16, 109-116, 2000.

Ellingwood, F., Ellingwood's Therapeutist, Jun. 14, 1908, 2(6), 32-33.

Elwood E.T., and D.G. Bolitho, Negative-Pressure Dressings in the Treatment of Hidradenitis Suppurative, *Annals of Plastic Surgery*, Jan. 2001, 46(1), 49-51.

Engdahl, O. and J. Boe, Quantification of Aspirated Air Volume reduces Treatment Time in Pneumothorax, *Eur. Respir, J.*, 1990, 3, 649-652.

Engdahl, O., et al., Treatment of Pneumothorax: Application of a Technique which Quantifies Air Flow Through the Chest Drain, *Adv. in Therapy*, May/Jun. 1988, 5(3), 47-54.

Erichsen, J.E., Science and Art of Surgery, *London: Longmans, Green, and Co.*, 1895, vol. 1, 258-259, and p. 289.

Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.

Fay, M.F., Drainage Systems: Their Role in Wound Healing, *AORN Journal*, Sep. 1987, 46(3), 442-455.

Fellin, R., Managing Decubitus Ulcers, *Nursing Management*, Feb. 1984. 29-30.

Fingerhut, A., et al., Passive vs. Closed Suction drainage after Perineal Wound Closure Following Abdominoperineal Rectal Excision for Carcinoma, *Dis Colon Rectum*, Sep. 1995, 926-932.

Finley, John M.,"Practical Wound Management," pp. 45, 127, 143, 149, 207, 1981

Firlit, C.F. and J.R. Canning, Surgical Wound Drainage: A Simple Device for Collection, *Journ. of Urology*, Aug. 1972, 108, p. 327.

Fisher, Jack, and R. W. Bert, Jr., A Technique for Skin Grafting Around Abdominal Wall Fistulas, *Annals of Plastic Surgery*, 11:6, Dec. 1983, 563-564.

Flanagan, et al., Optional Sump: Novel Use of Triple Lumen Closed Drainage System, *Anz. J. Surg.*, Nov. 2002, 72(11), 806-807, Abs. Downloaded from internet Nov. 30, 2003.

Fleck, C.A., When Negative is Positive: A Review of Negative Pressure Wound therapy, *Wound Care*, Mar./Apr. 2004, 20-25.

Flynn, M.E. and D.T. Rovee, Wound Healing Mechanisms, *Amer. Journ. of Nursing*, Oct. 1982, 1544-1556.

Fox, J.W. and G.T. Golden, The Use of Drains in Subcutaneous Surgical Procedures, *Amer. Journ. of Surg.* Nov. 1976, 132, 673-674.

Geiger Jones, E., et al., Management of an Iliostomy and Mucous Fistula Located in a Dehisced Wound in a Patient with Morbid Obesity, *J. WOCN*, Nov. 2003, 30(6), 351-356.

Gill, P., What is a Counter-Irritant? Name Three and the Method of Applying them, *Brit. Journ. Nurs.*, Jun. 1934, 142.

Goddard, L., Inflammation: Its Cause and Treatment, *Brit. Journ. Nurs.*, Jan. 1944, 2.

GOMCO Suction Equipment & Accessories Guide, Catalog, Apr. 2006, 20 pages.

Gouttefangeas, C. et al., Functional T Lymphocytes Infiltrate Implanted Polyvinyl Alcohol Foams During Surgical Wound Closure Therapy, *Clin. Exp. Immunol.* 2001, 124, 398-405.

Grabowski, S., Leczenie ran z zastosowaniem posicśnienia (wg Redona I Josta), *II Klinik Xhieuefxnej AM w Warszawie; klerownik: Prof. Dr. Z. Lapinski*, No. 1, 19-21 (in Polish).

Greene, M. A., et al. Laparotomy Wound Closure with Absorable Polyclycolic Acid Mesh, Surgery, Gynecology and Obsterics Mar. 1993; vol. 176, pp. 213-218.

Grishdevich, V. and N. Ostrovsky, Postburn Facial Resurfacing with a Split Ascending Neck Flap, *Plastic and Reconstructive Surgery*, Dec. 1993, 1384-1391.

Grobmyer, et al., High-Pressure Gradients Generated by Closed-Suction Surgical Drainage Systems, *Surg. Infect. (Larchmt)*, Autumn 2002, 3(3), 245-249, Abs., Downloaded Nov. 30 2003.

Grover, R. and R. Sanders, Recent Advances: Plastic Surgery, Clinical Review, *BMJ*, Aug. 8, 1998, 317, 397-400.

Gupta, S., Ed., Guidelines for Managing pressure Ulcers with Negative Pressure Wound Therapy, *Advances in Skin & Wound Care Suppl.*, Nov./Dec. 2004, 17(2), 1-16.

Gupta, S., Guidelines for Managing Pressure Ulcers with Negative Pressure Wound Therapy, Downloaded from internet http://proquest.uml.com on Feb. 3, 2006, 19 pages.

Gwan-Nulla, D.N, and R.S. Casal, Toxic Shock Syndrome Associated with the Use of the Vacuum-Assisted Closure Device, *Ann. Plast. Surg.*, Nov. 2001, 47(5), 552-554.

Hallstrom, B.R. and J.F. Steele, Postoperative Course after Total Hip Arthroplasty: Wound Drainage versus No Drainage, *Orthopaedic Review*, Jul. 1992, 847-851.

Hanbok för Hälso-Och Sjukvàrdsarbete Lokal Anvisning för Landstinget Sörland, Jan. 2001, 7 pgs, (in Swedish), Downloaded from Internet http://www.landstinget.sormland.se, Aug. 14, 2001, 7 pages.

Harkiss. K., Cheaper in the Long Run, *Community Outlook*, Aug. 1985, 19-22.

Harle, A. Z Orthop., 127: 513-517 (1989), "Schwachstellen herkommlicher Drainagen."

Harvard Pilgrim Health Care, Technology Assessment Policy, TA 6.29 Negative Pressure Wound therapy for Wound Healing, Dec. 2004, 1-6.

Hay, J., et al., Management of the Pelvic Space With or Without Omentoplasty after Abdominoperineal Resection for Carcinoma of the Rectum: a Prospective Multicenter Study, *Eur. J. Surg*, 1997, Abs.

Higgins, S., The Effectiveness of Vacuum Assisted Closure (VAC) in Wound Healing, *Centre for Clinical Effectiveness, Monash Medical Centre, Clayton VIC Australia*, Dec. 2003, 1-16.

Hilsabeck, J.R., The Presacral Space as a Collector of Fluid Accumulations Following Rectal Anastomosis: Tolerance of Rectal Anastomosis to Closed Suction Pelvic Drainage, Amer. Soc. of Colon and Rectal Surgeons vol. 25, No. 7, Oct. 1982.

Hilton, P., Surgical Wound Drainage: A Survey of Practices among Gynaecologists in the British Isles, *Br. Journ. of Obstetrics and Gynaecology*, Oct. 1988, 95, 1063-1069.

(56) References Cited

OTHER PUBLICATIONS

Hollis, H.W. and M.R. Troy, A Practical Approach to Wound care in patients with Complex Enterocutaneous Fistulas, *Surg., Gyn. & Obs.*, Aug. 1985, 161, 179-181.
Hugh, T.B., Abdominal Wound Drainage, *Med. Journ. of Australia*, May 4, 1987, 146, p. 505 (Correspondence).
Hulten, L., et al., Primary Closure of Perineal Wound after Proctocolectomy or Rectal Excision, *Acta Chir. Scand.*, 1971, 137, 467-469.
Hunt, T.K. and J.E. Dunphy, Eds., Fundamentals of Wound Management, *Appleton-Century-Crofts/New York*, 416-447, 1979.
Ilizarov, G.A., The Tension-Stress Effect on the Genesis and Growth of Tissues: Part II., *Clinical Orthopaedics and Related Research*, Feb. 1989, 239, 263-283.
Izmailov, S.G., et al., Device for Treatment of wounds and Abdominal Cavity, Contents, Surg. No. 8 1997, Downloaded from internet http://www.mediasphera.ru/surgery/97/8/e8-97ref.htm.
Izmailov, S.G., The Treatment of Eventrations with a Special Apparatus, Abstracts, Surg. No. 1 1997, Downloaded from internet, http://www.mediasphera.ru/surgery/97/1/el-97ref.htm.
Jeter, K., Closed Suction Wound Drainage System, *J. WOCN*, Mar./Apr. 2004, 51 (correspondence).
Kazan Medical Institute Doctors, A Gadget to Bring the Wound Edges Close, 78-79 (in Russian with English translation). Aug. 20, 1985.
KCI, Inc., Introducing the V.A.C. GranuFoam Silver Dressing, *Flyer*, 2 pages.
KCI, Inc., The V.A.C. System, 2000-2001 Brochure, 2 pgs.
KCI, Inc., Vacuum Assisted Closure (VAC) from Wound Healing, *Evidence Note 5, NHS Quality Improvement Scotland*, Nov. 2003, 1 page.
Keen, W.W., Ed., Surgery, Its Principles and Practice, 1919, W. B. Saunders Company, p. 56, excerpt, 1919.
Keith, C.F., Wound management Following Head and Neck Surgery, *Nursing Clinics of North America*, Dec. 1979, 14(4) 761-779.
Kennard, H.W., Bier's Hyperaemia, *Brit. Journ. Nurs.*, Mar. 20, 1909, 223.
Khil'Kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006.
Kiemele, L.J., et al., Catheter-Based Negative Pressure Wound Therapy: A New Paradigm of Care, *Nursing Home Wound Care consultative Service, Mayo Clinic*, Rochester, MN. 2 pages.
Kim, S.H., et al., Wangensteen Suction Drainage, apparatus in Neurosurgical Practice, *Dept. of Neurosurgery, Yonsei University of College of Medicine*, Seoul, Korea, 1975, 159-160, Abs, (in Korean and Abstract in English).
Kloth, L.C. and J.M. McCulloch, Wound Healing Alternatives in Management, 3rd Ed., Chap. 10, 339-352, 2002.
Knight, Marie Ray, A Second Skin for Patients with Large Draining Wounds, Nursing, Jan. 1976, p. 37, USA.
Kohlman, Phyllis A., et al, "Pouching Procedure to Collect Drainage From Around a Biliary Drainage Catheter," Ostomy/Wound Management, Nov./Dec. 1991, pp. 47-50, vol. 37.
Kordasiewicz, L.M., Abdominal Wound with a Fistula and Large Amount of Drainage Status after Incarcerate Hernia Repair, *J. WOCN*, May/Jun. 2004, 31(3), 150-153.
Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.
Larichev, A.B., Vacuum Therapy of Wounds and Wound Infection, 1st. Ed.. BlueSky Publishing, 2005.237 pgs.
Lee, J.H. and H.J. Yang, Application of Medifoam B® & Negative Pressure Therapy for the Auxiliary Treatment of Pressure Sore, *Dept. Plastic and Reconstructive Surg., College of Medicine, Eulji Univ.*, Daejeon, Korea, Abs, Sep. 31, 2004, 1 page.
Lockwood. C.B., Aseptic Surgery, Drainage, *Brit. Journ. Nurs.*, Mar. 26, 1904, 245.
Luchette, F.A., When Should the General Surgeon Leave the Abdomen Open?, Division of Trauma, Surgical Critical Care and Burns, Loyola University Medical Center, Maywood, Illinois., 37 pages (date N/A).
Lumley, J.S.P., et al., The Physical and bacteriological Properties of Disposable and Non-Disposable Suction Drainage Units in the Laboratory, *Br. J. Surg.*, 1974, 61, 832-837.
Lundvall, J. and T. Lanne, Transmission of Externally applied Negative pressure to the Underlying Tissue: A Study on the Upper Arm of Man, *Acta Physiol. Scand.* 1989, 136, 403-409.
Magee, C., et al., Potentiation of Wound Infection by Surgical Drains, *Amer. Journ. of Surg.*, May 1976, 131, 547-549.
Maitland and Mathieson, Suction Drainage, *Brit. J. Surg.*, Mar. 1970, 57(3), 195-197.
Mayo, C.W., The One-Stage Combined Abdominoperineal Resection for Carcinoma of the Rectum, RectoSigmoid and Sigmoid, *Surgical Clinics of North America*, Aug. 1939, Mayo Clinic No. 1011-1012.
McGuire, S., Drainage after Abdominal Section, *Br. Journ. of Nurs.*, Dec. 15, 1903, 447-449.
Medela, Inc., Pleupump MK II, Aug. 14, 2001, Brochure (in German). 12 pages.
Mendez-Eastman, S., Guidelines for Using Negative Pressure Wound Therapy, *Advances in Skin & Wound Care*, 14(6), Nov./Dec. 2001, 314-325.
Mendez-Eastman, S., When Wounds Won't Heal, *RN*, Jan. 1998, 2-7.
Meyer and Schmieden, Bier's Hyperemic Treatment, Fig. 69-70, 557.
Meyer and Schmieden, Bier's Hyperemic Treatment, Published 1908 W. B. Saunders Company, 44-65.
Miles, W. Ernest, "Technique of the Radical Operation for Cancer of the Rectum", The British Journal of Surgery,pp. 292-304, United Kingdom 1914-1915.
Miles, W.E., A Method of Performing Abdominoperineal Excision for Carcinoma of the Rectum and of the Terminal Portion of the Pelvic Colon, *The Lancet*, Dec. 19, 1908, 1812-1813.
Miller, M.S. and C. McDaniel, Treating a Pilonidal Cystectomy Abscess Wound with the BlueSky Medical Versatile 1™ Negative Pressure Wound Therapy, *The Wound Healing Center*, Terre Haute, Indiana, Case Study 2004-2006, 1 page.
Miller, M.S., Negative Pressure Wound Therapy: "A Rose by Any Other Name," *Ostomy/Wound Management*, Mar. 2005, 51(3), 44-49.
Milsom, I. and A. Gustafsson, An Evaluation of a Post-Operative Vacuum Drainage System, *Curr. Med. Res. Opin.* (1979), 6, 160-164.
Moloney, G. E., "Apposition and Drainage of Large Skin Flaps by Suction", ANZ Jourjal of Surgery vol. 26, Issue 3, Feb. 1957, pp. 173-179.
Morykwas, M.J., et al., Effects of Varying Levels of Subatmospheric Pressure on the Rate of Granulation Tissue Formation in Experimental Wounds in Swine, *Abs., Ann. Plast. Surg. 2001*, 47: 547.
Moserova, J. and E. Houskova, The Healing and Treatment of Skin Defects, 1989, 116-143.
Moss, W., What is Cellulitis? Describe Some Forms of Treatment You Would Expect to be Used for Cellulitis of the Arm, *Brit. Journ. Nurs.*, Nov. 1935, 282.
Mulder, G.D., Ed., et al., Clinicians' Pocket Guide to Chronic Wound Repair, *Wound Healing Publications*, Spartanburg, SC, 1991, 54-55.
Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.
Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.
Nakayama, Yoshio, et al., A New Method for Dressing of Free Skin Grafts, New Method for Free Skin Grafting, vol. 86, No. 6 Jun. 12, 1990.
Nasser, A.N., The Use of the Mini-Flap Wound Suction Drain in maxillofacial Surgery, *Annals of the Royal College of Surgeons of England*, 1986, 68, 151-153.
Navsaria, P.N., et al., Temporary Closure of Open Abdominal Wounds by the Modified Sandwich-Vacuum Pack Technique, *Br. Journ. Surg.*, 2003, 90, 718-722.

(56) References Cited

OTHER PUBLICATIONS

Nghiem, D.D., A Technique of Catheter insertion for Uncomplicated Peritoneal Dialysis, *Surgery, Gynecology & Obstetrics*, Dec. 1983, 157, 575-576.

Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on The Open Abdomen in General Surgery—How Do You Close the Abdomen When You Can't—Bostom Marriott Copley Place Hotel, Boston, MA Apr. 26, 2004.

Nightingale, K., Making Sense of wound Drainage, *Nursing time* Jul. 5, 1989, 85(27), 40-42.

Noblett, E.A., What is an Empyema? What Operations are Undertaken for its Relief, and What Have You to Say About the After-Nursing?, *Brit. Journ. Nurs.*, Apr. 29, 1916, 375.

Nursing75, Wound Suction: Better Drainage with Fewer Problems, Nursing, vol. 5, No. 10, Oct. 1975, pp. 52-55.

O'Byrne, C., Clinical Detection and Management of Postoperative Wound Sepsis, *Nursing Clinics of North American*, Dec. 1979, 14(4), 727-741.

Ohotskii, V.P., et al., Usage of Vacuum Suction During the Primary Surgical Debridement of Open Limb Injuries, *Sovetskaya Medicina*, 1973, Jan. 17-20 (in Russian with English translation).

Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.

Orgill, D. P., et al., Microdeformational Wound Therapy—A New Era in Wound Healing, *Tissue Engin. and Wound Healing Laboratory, Brigham and Women's Hospital, Business Briefing: Global Surgery—Future Direction 2005*, 22.

Orgill, D., et al., Current Concepts and Approaches to Wound Healing, *Critical Care Medicine*, Sep. 1988, 16(9), 899-908.

Orgill, D.P., et al., Guidelines for Treatment of Complex Chest Wounds with Negative Pressure Wound Therapy, *Wounds, A Compendium of Clinical Research and Practice, Suppl. B*, Dec. 2004, 1-23.

Oringer et al., "Management of Wounds in Patients with Complex Enterocutaneous Fistulas," Surgery, Gynecology, & Obstetrics, Jul. 1987, vol. 165, pp. 79-80.

Oschsner, A.J., Surgical Diagnosis and Treatment, 1921, 11, 266-269.

Parker, M.J. and C. Roberts, Closed suction Surgical Wound Drainage after Orthopaedic Surgery, *Cochran Database of Systematic Review* 2005, 3, 3 pages.

Parulkar, B.G., et al., Dextranomer Dressing in the Treatment of Infected Wounds and Cutaneous Ulcers, *J. Postgrad. Med.*, 1985, 31(1), 28-33.

Penman, M., What Are the Signs and Symptoms of Gallstones? What Instruments Would You have Ready for the Operation? How Would You Nurse a Case After Operation?, *Brit. Journ. Nurs.*, Aug. 9, 1919, 88.

Pham, C., et al., Vacuum-Assisted Closure for the Management of Wounds: An Accelerated Systematic Review, *Asernip-Accelerated Review of Vacuum Assisted Wound Closure, Report No. 27*, Dec. 2003. 1-52.

Precision Medical, Power VAC+ Intermittent Aspirator, http://precisionmedical.com Downloaded from internet Apr. 10, 2006, 2 pages.

Putney F. Johnson, "The Use of Continuous Negative Pressure after Laryngectomy and Radical Neck Dissection", Surgery, Gynecology & Obstetrics, Aug. 1956, pp. 244-246, USA.

Raffl, Arthur B., "Use of Negative Pressure Under Skin Flaps After Radical Mastectomy, "Dept. of Surgery, State Univ. of N.Y., College of Medicine, Syracuse, NY, Submitted for publication Apr. 1953, p. 1048, USA.

Rammensee, H.G., Untersuchung der Lymphozytenin filtrate in Implantierte PVA-Schwämme nach der Therapie infizierter Wunden mit Vakuumversiegelung, Aus dem Interfakulatären Institut für Zellbiologie der Universität Tübingen Abeilung Immunologie Abteilungsleter, 2004, 119 pgs.

Redon, H. and J. Troques, La Fermeture Sous Depression des Plaies Etendues, *Academe de Chirurgie*, Mar. 1954, 304-306. (in French).

Redon, H., Closure of Large Wounds under a Partial Vacuum, Paris, *Notes on Practical Medicine*, published under L. Rouques, 1-3.

Reedy, J., The Science Behind Wound Healing, *UW Health Sciences/ UW Medicine News and Community Relations*, Winter/Spring 2005, 4 pages.

Reference Handbook of the Medical Sciences, *Hyperaemia*, 553.

Reid, Daniel P., Information on Cupping or Using Suction Cups on Wounds and for Healing Purposes, *Chinese Herbal Medicine*, 2 pages.

Reimann, D., et al., Successful Treatment Due to Vacuum Seal Technique of a Severe Scedosporium Apiospermum Skin Infection in a Renal Transplant Recipient, *Nephrol. Dial. Transplant*, 2004, 19 (1), 245-248.

Richter, Treatment of Inflammatory Conditions of the Skin with Hot Baths, *Brit. Journ. Nurs.*, Aug. 25, 1906, 149.

Roberts, R.H., et al., Randomised Trial of Medinorm LVS and Surgivac Drainage System after Operations for Breast Cancer May 1999, *Amer. Journ. Surg.*, Feb. 1997, 2 pgs.

Robertson, "The Influence upon Wound Contraction of a Negative Interstitial Fluid Pressure Within Granulation Tissue," Journal of Anatomy, 1969, vol. 105, No. 1, pp. 189.

Rodrigo, J.J., et al., The Effect of Varying Degrees of Suction Pressure on Drainage of Hematomas, *Dept. of Orthopaedic Surgery, University of California*, David, Sacraments, California, 9 pages (date N/A).

Rosser, C.J., et al., A New Technique to Manage Perineal Wounds, *Infections in Urology*, Mar./Apr. 2000, 4 pgs.

Royle, G.T. and B.J. Britton, Disposable Drains, *Articles of the Royal College of Surgeons of England*, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, *burns*, 1988, 14(4), 323-325.

Samson, D., et al., Wound-Healing Technologies: Low-Level Laser and Vacuum-Assisted Closure, *Evidence report/Technology Assessment*, No. 111, Dec. 2004, AHRQ Publication No. 05-E005-2 97 pages.

Sandahl, L., Slides at Geisinger Medical Center, Danville, PA, Apr. 10, 1990, Correspondence, 4 pages.

Schaffer, D.B., Closed Suction Wound Drainage, Nursing97, Nov., Downloaded from internet www.springnet.com, 62-64. 1997.

Schumann, D., Preoperative Measures to Promote Wound Healing, *Nursing Clinics of North America*, Dec. 1979, 14(4), 683-699.

Schwab, Peter M. and Kelly, Keith A., "Primary closure of the Perineal Wound After Proctectomy," Mayo Clinic Proc., Mar. 1974, pp. 176-179, vol. 49, US.

Scott, F., Babies in Bottles, *Advance for Resp. Care Practitioners*, Nov. 23, 1992, 2 pgs.

Senyutovich, R.V., Napkin Preventing Abdominal Contamination in Perforamance of Colonic Anastomosis, Abstracts, Downloaded from internet, http://www.mediasphera.ru/surgery/97/1/el-97ref.htm—1997, 1 page.

Shaer, W.D., et al., Inexpensive Vacuum-Assisted Closure Employing a Conventional Disposable Closed-Suction Drainage System, *Plastic and Reconstructive Surgery*, Jan. 2001, 292.

Sheen, A.W., Some Experiences of Shell Wounds in the Present War, (excerpt), *Brit. Journ. Nurs.*, Jan. 16, 1915, 42.

Sheppard, M.D., "Sealed Drainage of Wounds", The Lancet, Jun. 14, 1952, pp. 1174-1176.

Smith, L.A., et al., Vacuum Pack Technique of Temporary Abdominal Closure: A Four-Year Experience, *Amer. Surg.*, Dec. 1997, 63(12), 1102-1108.

Spahn, Slide presented at the WOCN meeting in Ontario, California, Sep. 2001.

Specific Inflammations, Diseases of the Skin, 549-550.

Spengler, Michael D., el al, "Performance of Filtered Sump Wound Drainage Tubes", Surgery, Gynecology & Obstetrics, Mar. 1982, pp. 333-336, vol. 54, USA.

(56) References Cited

OTHER PUBLICATIONS

Stewart, M. F., et al., Cleaning v Healing, *Community Outlook*, Aug. 1985, 22-26.
Surgidyne, Closed Systems for Management of Wound Drainage, Brochure and Catalog, Downloaded from internet, www.sterion.com, 6 pages (date N/A).
Swanson, L., Solving Stubborn-Wound problem Could Save Millions, Team Says, *JAMC*, Feb. 23, 1999: 160(4), p. 556.
Taylor, Virginia, Meeting the Challenge of Fistulas & Draining Wounds, Nursing, Jun. 1980, pp. 45-51, USA.
Tennant, C. E., "The Use of Hyperemia in the Postoperative Treatment of Lesions of the Extremities and Thorax," Jour. A. M. A., May 8, 1915, pp. 1548-1549.
Tenta, L.T., et al., Suction Drainage of Wounds of the Head and Neck, *Surg. Gyn. & Ob.*, Dec. 1989, 169, p. 558.
The Bier Treatment, *Brit. Journ. Nurs.*, Jun. 6, 1908, 452.
The British Journal of Nursing, Nov. 4, 1911, 368.
Thomas, Stephen "Wound Management and Dressings" 35-42 (1990).
Tittel, K. and G. Tolksdorff, Forum: VariDyne—Neue Standard in der Postoperative Wunddrainage (New Standards in Postoperative Wound Drainage), *Unfallchirurgie*, 1988 14(2), 104-107 (in German with English Translation).
Tuberculous Joints, *Nursing record & Hospital World*, Apr. 28, 1894, 280.
Unknown, "The RN Magazine/University of California Continuing Education Curriculum; Examination on 'To heal a draining wound'", RN, Mar. 1982, p. 36, USA.
Urschel, J.D., et al., The Effect of Mechanical Stress on Soft and Hard Tissue Repair; A Review, *Br. Journ. Plast. Surg.*, 1988, 41, 182-186.
Usypov, Y.N. and M.V. Ephfanov, Active Drainage of wounds, Dept. of Hospital Surgery, Army Medical Academy, Leningrad, *Vestnik Chirurgia* Apr. 1987 Edition, 42-45 (in Russian with English translation).
Valenta, A.L., Using the Vacuum Dressing Alternative for Difficult Wounds, *AIN*, Apr. 1994, 44-45.
Van Heurn, L.W.E. and P.R.G. Brink, Prospective Randomized Trial of High versus Low Vacuum Drainage after Axillary Lymphadenectomy, *Br. Journ. Surg.* 1995, 82, 931-932.
Van Way III, C.W., Prevention of Suction-Induced Gastric mucosal damage in Dogs, *Critical Care Medicine*, Aug. 1987, 15(8), 774-777.
Varley, G.W. and S.A. Milner, Wound Drains in Proximal Femoral Fracture Surgery: A Randomized prospective Trial of 177 Patients, *J. R. Coll. Surg. Edinb.*, Dec. 1995, 40, 416-418.
Wackenfors, A., et al., Effects of Vacuum-Assisted Closure Therapy on Inguinal Wound Edge Microvascular Blood Flow, *Wound Rep. Reg*, 2004, 12, 600-606,
Warren, J.C. and A.P., Gould, Ed., The International Text-Book of Surgery, 1902, 1, 70-79.
Waymack, J. P., et al.: "An evaluation of Aquaphor Gauze dressing in burned children", Burns Include therm Inj. Aug. 1986;12(6):443-8.
Wayne, M.A., Cook Pneumothorax Catheter Set, Wayne Pneumothorax Catheter Set, *Cook Critical Care, Cook Incorporated 1997*, 3 pgs.
Westaby, S., Wound Care No. 11, *Nursing Times*, Jul. 21, 1982, 41-48.
White, R.A., et al., Vacuum-Assisted Closure Complicated by Erosion and Hemorrhage of the Anterior Tibial Artery, *Journal of Orthopaedic Trauma*, Jan. 2005, 19(1), 56-59, Abs. Cited in BlueSky internal email dtd. Nov. 9, 2005.
Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from internet Nov. 30, 2003.
Windows on Medical Technology, Vacuum-Assisted Wound Closure for Chronic and Acute Wounds, , *ECRI Health Technology Assessment Information Service*, Oct. 2000, 38, 1-21.
Witkowski, J.A. and Parish, L.C., Synthetic Dressings: Wound Healing in the '80s, *Hospital Therapy*, Nov. 1986, 75-84.
Wolthuis, Roger A., et al, "Physiological Effects of Locally Applied Reduced Pressure in Man," Physiological Reviews, Jul. 1974, pp. 566-595 vol. 54, No. 3, USA.
Worth, M.H. and H.W. Andersen, The Effectiveness of Bacterial Filtration in Vented Wound Drains, *Journ. of Surg. Research*, 1979, 27, 405-407.
Wu, P., et al., In Vitro Assessment of Water Vapour Transmission of Synthetic Wound Dressings, *Biomaterials*, 1995, 16(3), 171-175.
Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm: 1 page.
Zamierowski, David S., Letter: "All Foam Sponges are not Equal in Vacuum Dressings," British Journal of Plastic Surgery, 1999, 52, 78-81, p. 79, United Kingdom.
Zhetimkarimov, D.S. and V.K. Ostrovsky, The Applied Significance of Anatomic Pecularities of Greater Momentum, Contents, Surg. No. 6, 1997, Downloaded from internet http://www.mediasphera.ru/surgery/97/6/e6-97ref.htm, 1 page.
US 6,216,701, 04/2001, Heaton et al. (withdrawn)

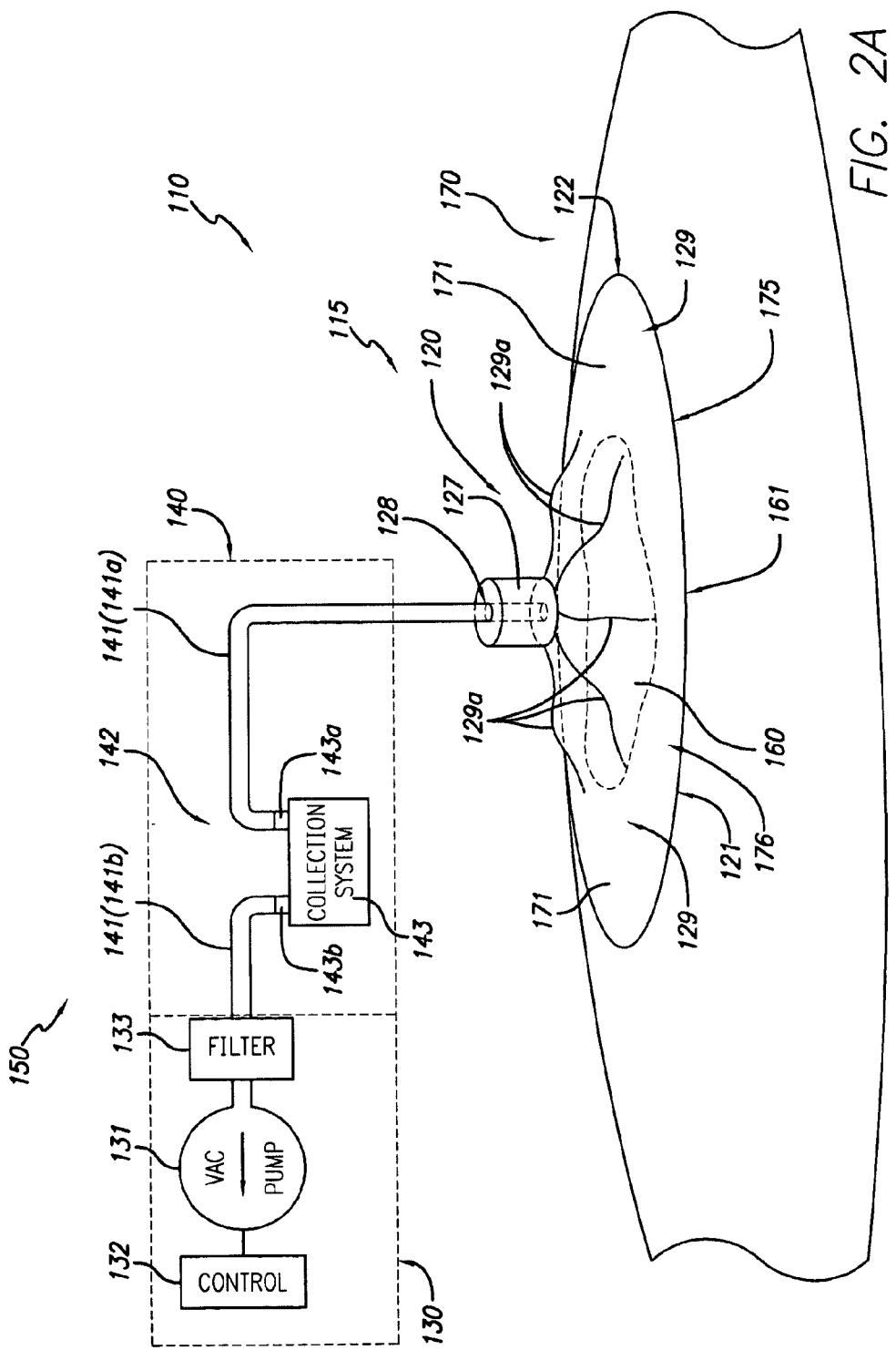

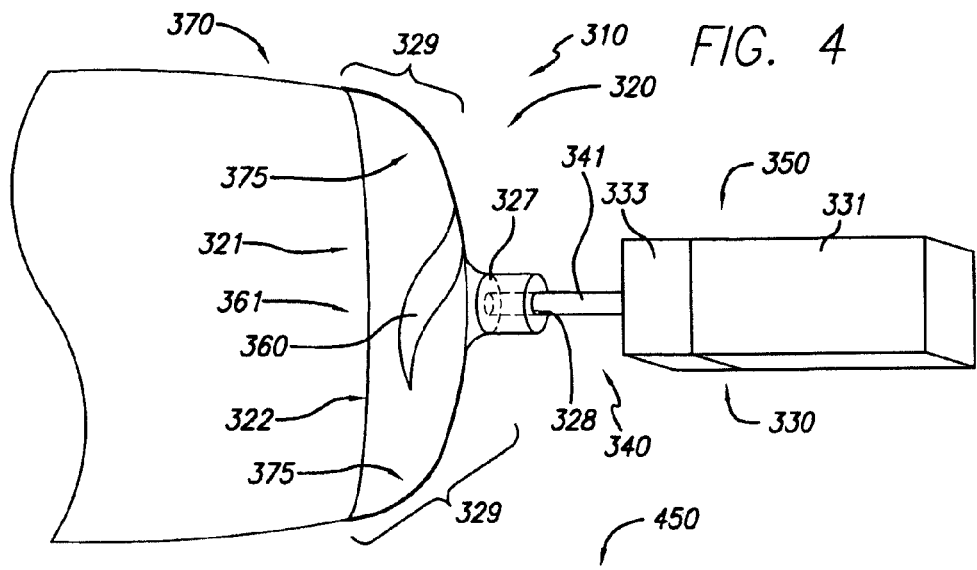
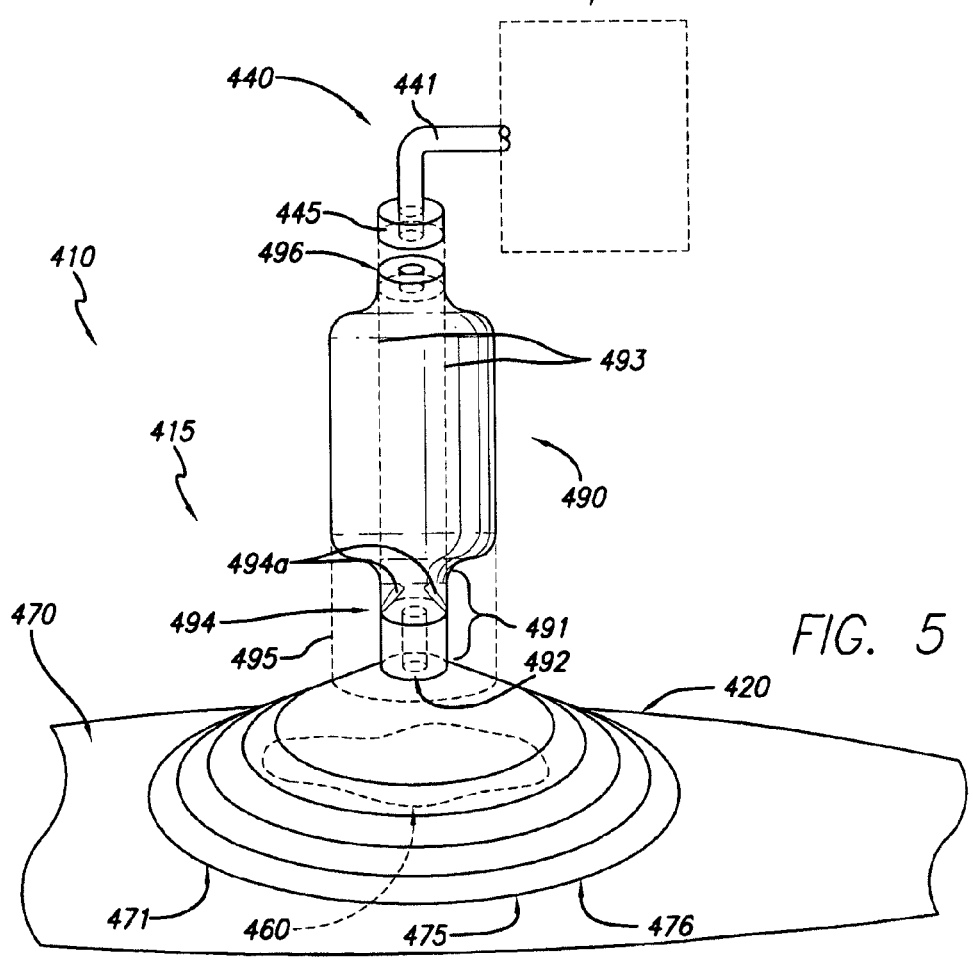

FLEXIBLE REDUCED PRESSURE TREATMENT APPLIANCE

CROSS-REFERENCE TO RELATED APPLICATIONS

This application is a continuation of U.S. patent application Ser. No. 12/719,767, entitled FLEXIBLE REDUCED PRESSURE TREATMENT APPARATUS, filed Mar. 8, 2010, which is a divisional of U.S. patent application Ser. No. 11/064,813, entitled FLEXIBLE REDUCED PRESSURE TREATMENT APPARATUS, filed on Feb. 24, 2005, which claims the benefit of U.S. provisional application No. 60/573,655, entitled WOUND DRAINAGE MEMBRANE DEVICE, and filed on May 21, 2004. The contents of the aforementioned applications are hereby incorporated by reference in their entireties as if fully set forth herein. The benefit of priority to the foregoing applications is claimed under the appropriate legal basis, including, without limitation, under 35 U.S.C. §119(e).

BACKGROUND OF THE INVENTION

Field of the Invention

The present invention generally relates to treatment of wounds, and more specifically to an improved apparatus and method for treating all or a portion of a wound on a body by applying reduced pressure to the portion of the wound for which treatment is desired. In this context, the terms "wound" and "body" are to be interpreted broadly, to include any body part of a patient that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed by the present inventor with the U.S. Patent and Trademark Office on Aug. 28, 2003. The disclosure of this U.S. patent application is incorporated herein by reference. Another system is disclosed in a U.S. patent application entitled "Improved Reduced Pressure Wound Treatment Appliance," which was filed by the present inventor with the U.S. Patent and Trademark Office on or about Dec. 30, 2004. The disclosure of this U.S. patent application is also incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. However, the covers currently known and used in the art have a number of disadvantages. For example, in one version they tend to be in the form of a flexible sheet of material that is placed over the wound and sealed to the surrounding tissue using an adhesive, adhesive tape, or other similar means. As tissue swelling in the area of the wound decreases during the healing process, the adhesive may begin to stretch the surrounding tissue, as well as tissue within the wound, resulting in discomfort and pain to the patient. This may necessitate more frequent cover changes, increasing the time medical staff must expend in treating the wound. This additional time, of course, also tends to increase the expense involved in treating the wound. In addition, these types of covers can typically only be used where there is normal tissue adjacent to the wound to which the adhesive seal can be attached. Otherwise, the seal must be made in a portion of the area of the wound, and exudate from the wound tends to break the seal so that reduced pressure cannot be maintained beneath the wound cover. Thus, such covers (and many other covers requiring adhesive seals) may typically only be used to treat an entire wound, as opposed to only a portion of a wound. Further, the adhesive seal creates discomfort for the patient when the sheet cover is removed. In other versions, the covers tend to be rigid or semi-rigid in nature so that they are held away from the surface of the wound. In these versions, the covers are sometimes difficult to use because the shape and contour of the patient's body in the area of the wound do not readily adapt to the shape of the cover. In such cases, additional time is required for the medical staff to adapt the cover for its intended use. This also increases the expense of wound treatment. In addition, it is also often necessary to use an adhesive, adhesive tape, or other similar means to seal the rigid or semi-rigid cover to the tissue surrounding the wound. In these instances, the same disadvantages discussed above with respect to the first version also apply to this version as well. In still other cases, the rigid and semi-rigid covers must be used with padding in the area where the cover is adjacent to the patient to prevent the edges of the cover from exerting undue pressure on the tissue surrounding the wound. Without the padding, the patient may experience pain and discomfort. The additional padding, which may make the cover itself more expensive, may also take a greater amount of time to place on the patient for treatment purposes. These covers may also have the problem of placing tension on the surrounding tissue as the swelling in the area of the wound decreases during the healing process. In yet another version, covers are constructed of combinations of flexible materials and rigid materials. In these versions, a flexible member, such as a flexible sheet, is typically supported by a rigid or semi-rigid structure that is either placed between the flexible member and the wound or in the area above and outside the flexible member. In either case, the flexible member must usually be sealed to the tissue surrounding the wound using an adhesive, adhesive tape, or other similar means. This seal creates the same problems described above. In addition, the same problems described above with respect to rigid and semi-rigid structures are also often present. In all of the versions described above, it may be difficult to tell if reduced pressure in the area of the wound under the cover has been lost because the cover itself does not generally provide a visual clue of such loss.

Therefore, there is a need for a reduced pressure wound treatment system that has a means to enclose all or a portion of a wound without the need for an adhesive seal. There is also a need for such enclosing means to be flexible, so that it adapts to changing shapes and contours of the patient's body as wound healing progresses. Further, there is a need for an enclosing means that is adaptable to a wide variety of patient body shapes and contours. There is also a need for an enclosing means that is simple to apply to the patient's body, and simple to remove from the patient's body. Such enclosing means would also take less time to apply and remove, reducing the expense involved in wound treatment. There is also a need for an enclosing means that is relatively inexpensive, while meeting the needs described above. In addition, there is a need for an enclosing means that may be used within the wound (or a portion thereof), without the need to seal the enclosing means to normal tissue surrounding the wound. Further, there is a need for an enclosing means that flexes with movement of the portion of the body surrounding the wound, without the need for an adhesive seal or rigid or semi-rigid structure. Finally, there is a need for an enclosing means that provides a visual clue of loss of reduced pressure in the area of the wound under the enclosing means.

SUMMARY OF THE INVENTION

The present invention is directed to a reduced pressure wound treatment appliance and methods that satisfy the needs described above. As described in greater detail below, they have many advantages over existing reduced pressure wound treatment apparatus and methods when used for their intended purpose, as well as novel features that result in a new reduced pressure wound treatment appliance and methods that are not anticipated, rendered obvious, suggested, or even implied by any of the prior art apparatus or methods, either alone or in any combination thereof.

In accordance with the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In a first aspect of a first version of the present invention, the wound treatment appliance is comprised of an impermeable flexible overlay and reduced pressure supply means, which are described in more detail below and are used to connect the flexible overlay to a reduced pressure supply source that provides a supply of reduced pressure to the flexible overlay. In this first aspect of the first version of the invention, the flexible overlay is adapted to be placed over and enclose all or a portion of a wound on the surface of the body of a patient. The flexible overlay is also adapted to maintain reduced pressure under the flexible overlay in the area of the wound. The flexible overlay collapses in the approximate direction of the area of the wound to be treated when reduced pressure is supplied to the volume under the flexible overlay in the area of the wound. This collapse causes the formation of an approximately hermetic seal (described in more detail below) between the flexible overlay and the body in the area of the wound. In some embodiments of this first aspect of the first version of the invention, the flexible overlay is further comprised of an interior surface facing the area of the wound to be treated, wherein the surface area of the interior surface is greater than the surface area of the portion of the body to be enclosed by the flexible overlay. In other embodiments of this first aspect of the first version of the invention, the flexible overlay is further comprised of a bottom portion having an approximately elongated conical shape with an approximately elliptically-shaped open end at the base of the elongated conical bottom portion. In these embodiments, the approximately elliptically-shaped open end at the base is sized to be placed over and enclose the area of the wound to be treated. In yet other embodiments of this first aspect of the first version of the invention, the flexible overlay (as opposed to only the bottom portion thereof) has an approximately elongated conical shape having an approximately elliptically-shaped open end at its base. In these embodiments, the approximately elliptically-shaped perimeter of the open end at the base of the flexible overlay is positioned over all or a portion of the wound on the surface of the body. In some of these embodiments, the flexible overlay further comprises a port located approximately at the apex of the elongated conically-shaped flexible overlay. In these embodiments, the reduced pressure supply means is operably connected to the port. In yet other embodiments of this first aspect of the first version of the invention, the flexible overlay is comprised of at least three cover portions, each of such cover portions being approximately triangular in shape. One point of each of the at least three triangular-shaped cover portions are joined to form an apex of the flexible overlay and one side of each at least three triangular-shaped cover portions adjacent to the apex is joined to an adjacent side of another of such at least three triangular-shaped cover portions so that the bases of the at least three triangular-shaped cover portions form an opening sized to be placed over and enclose the area of the wound to be treated. In some of these embodiments, the flexible overlay is further comprised of a port located approximately at the apex of the flexible overlay and the reduced pressure supply means is operably connected to the port. In still other embodiments of this first aspect of the first version of the invention, at least one fold forms in the surface of the flexible overlay when it collapses, so that fluids aspirated by the wound flow along the at least one fold to the reduced pressure supply means, where they are removed from the flexible overlay by means of the reduced pressure supply means cooperating with the reduced pressure supply source. In other embodiments, the appliance further comprises supplemental sealing means, which are described in more detail below, to form a seal between the flexible overlay and the body in the area of the wound. In yet other embodiments, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the flexible overlay in the area of the wound by means of the suction drain. The suction drain extends from the reduced pressure supply means into the volume under the flexible overlay in the area of the wound.

In a second aspect of the first version of the present invention, the wound treatment appliance is comprised of a wound treatment device and a vacuum system. In this second aspect of the first version of the invention, the vacuum system is further comprised of a reduced pressure supply source that provides a supply of reduced pressure and reduced pressure supply means to operably connect the wound treatment device to the reduced pressure supply source, so that the volume under the wound treatment device in the area of the wound is supplied with reduced pressure by the reduced pressure supply source. In various embodiments of this second aspect of the first version of the invention, the wound treatment device and the reduced pressure supply means may generally have substantially the same structure, features, characteristics and operation as the appliance described above in connection with the first aspect of the first version of the invention.

In some embodiments of this second aspect of the first version of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments of this second aspect of the first version of the invention, the reduced pressure supply means is comprised of flexible tubing. In other embodiments, the reduced pressure supply means is further comprised of a collection system that is operably positioned between the wound treatment device and the reduced pressure supply source. In some of these embodiments, the collection system comprises a container to receive and hold fluid aspirated from the wound and pressure halting means to halt the application of reduced pressure to the wound when the fluid in the container exceeds a predetermined amount. In other embodiments of this second aspect of the first version of the invention, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments of this second aspect of the first version of the invention, the wound treatment appliance further comprises tissue protection means, which are described in more detail below, to protect and strengthen the body tissue that is adjacent to the flexible overlay at the wound site. In some of these embodiments, the tissue protection means is a hydrocolloid material.

In a third aspect of the first version of the invention, the wound treatment appliance is comprised of a wound treatment device, a vacuum system, and wound packing means, which are described in more detail below, that are positioned between the wound treatment device and the portion of the wound to be treated. In various embodiments of this third aspect of the first version of the invention, the wound treatment device and the vacuum system may generally have substantially the same structure, features, characteristics and operations as the wound treatment device and the vacuum system, respectively, described above in connection with the second aspect of the first version of the invention. In this third aspect of the first version of the invention, the flexible overlay of the wound treatment device is placed over all or a portion of the wound and the wound packing means when the flexible overlay is positioned on the surface of the body at the wound site. In some embodiments of this third aspect of the first version of the invention, the wound packing means is comprised of absorbent dressings, antiseptic dressings, nonadherent dressings, water dressings, or combinations of such dressings. In some of these embodiments, the wound packing means is preferably comprised of gauze or cotton or any combination of gauze and cotton. In still other embodiments, the wound packing means is comprised of an absorbable matrix adapted to encourage growth of the tissue in the area of the wound under the flexible overlay into the matrix. The absorbable matrix is constructed of an absorbable material that is absorbed into the epithelial and subcutaneous tissue in the wound as the wound heals. Because of the absorbable nature of the absorbable matrix, the matrix should require less frequent changing than other dressing types during the treatment process. In other circumstances, the matrix may not need to be changed at all during the treatment process. In some of these embodiments, the absorbable matrix is comprised of collagen or other absorbable material. In some embodiments of this third aspect of the first version of the invention, the appliance further comprises a suction drain and suction drain connecting means, which are described in more detail below, to operably connect the reduced pressure supply means to the suction drain so that the suction drain is in fluid communication with the reduced pressure supply means and reduced pressure is supplied to the volume under the impermeable flexible overlay in the area of the wound by means of the suction drain. In these embodiments, the suction drain extends from the reduced pressure supply means into the volume under the impermeable flexible overlay in the area of the wound. In some of these embodiments, the suction drain is further comprised of a distal end portion and the distal end portion has at least one perforation in the surface thereof. In some of these embodiments, the distal end portion of the suction drain is positioned within the interior volume of the wound packing means.

In a fourth aspect of the first version of the invention, the wound treatment appliance is comprised of a wound treatment device and a vacuum system. In various embodiments of this fourth aspect of the first version of the invention, the wound treatment device is comprised of an impermeable overlay and a seal. The impermeable overlay is sized to be placed over and enclose the area of the wound to be treated and is adapted to maintain reduced pressure in the area of the wound to be treated. The seal seals the impermeable flexible overlay to the body in the area of the wound in a manner so that reduced pressure is maintained under the impermeable overlay in the area of the wound to be treated. In addition, in the various embodiments of this fourth aspect of the first version of the invention, the vacuum system is comprised of a suction bulb, which may (but not necessarily) provide a source of reduced pressure, and reduced pressure supply means, which are described in more detail below, to operably connect the impermeable overlay to the suction bulb, so that the area of the wound under the impermeable overlay may be supplied with reduced pressure by the suction bulb. In some embodiments of this fourth aspect of the first version of the invention, the impermeable overlay is comprised of a rigid or semi-rigid wound cover. In other embodiments, the impermeable overlay is comprised of a flexible wound cover. In some of these embodiments, the flexible wound cover may be comprised of a flexible overlay that has substantially the same structure, features, characteristics and operation as the flexible overlay described above in connection with the first aspect of this first version of the invention. In some embodiments of this fourth aspect of the first version of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms aspirated from the wound or fluids aspirated from the wound or both. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the second and third aspects of the first version of the invention.

A fifth aspect of the first version of the present invention discloses a method of treating a wound on a body. In one embodiment of this fifth aspect of the first version of the invention, the method comprises the following steps. First, positioning an flexible overlay on the body over the area of the wound to be treated, wherein the flexible overlay is sized to be placed over and enclose the area of the wound to be treated and adapted to maintain reduced pressure in the area of the wound to be treated. Second, operably connecting the flexible overlay with a vacuum system for producing reduced pressure in the volume under the flexible overlay in the area of the wound to be treated. Third, collapsing the flexible overlay in the approximate direction of the wound when reduced pressure is supplied to the volume under the flexible overlay in the area of the wound so that an approximately hermetic seal (described in more detail below) is formed between the impermeable flexible overlay and the body in the area of the wound. Fourth, maintaining the reduced pressure until the area of the wound being treated has progressed toward a selected stage of healing. In other embodiments of this fifth aspect of the first version of the invention, the method further comprises the step of placing tissue protection means on the tissue of the body that is to be approximately adjacent to the flexible overlay, such step being performed prior to positioning the flexible overlay over the area of the wound to be treated. The tissue protection means, which is described in more detail below, protects and strengthens the tissue of the body adjacent to the flexible overlay at the wound site. In yet other embodiments of this fifth aspect of the first version of the invention, the method further comprises the step of placing wound packing means (described in more detail above) between the wound and the flexible overlay in the area of the wound to be treated, such step being performed prior to positioning the flexible overlay over the area of the wound to be treated. In still other embodiments of this fifth aspect of the first version of the invention, the vacuum system is comprised of a suction bulb and the method further comprises the step of squeezing the suction bulb to reduce its volume and then releasing the suction bulb, so that reduced pressure is produced in the volume under the flexible overlay in the area of the wound. In other embodiments of this fifth aspect of the first version of the invention, the reduced pressure under the impermeable overlay in the area of the wound is in the range from approximately 20 mm of Hg below atmospheric pressure to approximately 125 mm of Hg below atmospheric pressure. In still other embodiments of this fifth aspect of the first version of the invention, the reduced pressure is applied in a cyclic nature, the cyclic nature providing alternating time periods of application of reduced pressure and without application of reduced pressure.

As is illustrated in the detailed descriptions herein, the wound treatment appliance of the present invention meets the needs discussed above in the Background section. For example, in the preferred embodiment of a flexible overlay having a bottom portion with an approximately elongated conical shape, the flexible overlay is placed over and encloses all or a portion of the wound. When the flexible overlay is enclosing all or a portion of the wound, the portions of the flexible overlay positioned adjacent to the surface of the body at the wound site are at (or can be deformed to be at) a relatively acute angle relative to such surface of the body. When reduced pressure is applied to the area under the flexible overlay, the flexible overlay is drawn downward, collapsing the flexible overlay in the approximate direction of the wound. As the flexible overlay collapses, the portions of the flexible overlay adjacent to the perimeter of the opening of the flexible overlay are drawn tightly against the surface of the body at the wound site, thus forming an approximately hermetic seal. References to an "approximately hermetic seal" herein refer generally to a seal that is gas-tight and liquid-tight for purposes of the reduced pressure treatment of the wound. It is to be noted that this seal need not be entirely gas-tight and liquid-tight. For example, the approximately hermetic seal may allow for a relatively small degree of leakage, so that outside air may enter the volume under the flexible overlay in the area of the wound, as long as the degree of leakage is small enough so that the vacuum system can maintain the desired degree of reduced pressure in the volume under the flexible overlay in the area of the wound. In some uses where the collapsing flexible overlay may not produce an approximately hermetic seal that is solely capable of maintaining the reduced pressure in the volume under the impermeable overlay in the area of the wound, it may be necessary to provide supplemental sealing means, which are described in more detail below, and which are used to provide a seal between the portions of the flexible overlay and the body where the approximately hermetic seal is not adequate. As a result, the flexible overlay is simple to apply to the patient. There is also often no need for any other sealing means in most cases, which means that there is usually no need for medical staff to take the time to make a separate seal. Even where the geometry of the surface of the body surrounding the wound may require that supplemental sealing means be used to provide some limited assistance to ensure a seal, the amount of such assistance (such as by applying an adhesive) is limited, especially when compared to current covers in the art. In addition, as swelling of tissue at the wound site decreases, the flexible nature of the flexible overlay allows it to further deform to conform to the changing shape and contours at the wound site. This prevents the patient from being discomforted as the swelling decreases. It also reduces the need to change the covering over the wound as healing progresses. This is generally not true in cases involving flexible, semi-rigid and rigid covers that exist in the art. For example, even where semi-rigid and rigid covers do not utilize an adhesive seal and rely solely upon the reduced pressure to hold them in place, they do not generally change shape enough to flex with substantial changes in the shape and contour of the surrounding body surface. Thus, they may not be appropriate for use with body portions that are subject to such changes, while the flexible nature of the flexible overlay, along with its increased surface area that can bend and flex, allow it to be used in such circumstances without the need for an adhesive seal. In the same way, the flexible overlay may generally be used for unusual geometries of the body at or surrounding the wound because of the overlay's flexible nature and relatively large surface area. In contrast, flexible sheets and semi-rigid and rigid covers may require substantial modification and means to provide an adequate seal. In addition, such covers may require that the patient be partially or wholly immobilized during the treatment process to avoid movement in the area of the body surrounding the wound to avoid breaking the seal. And such covers must usually be sealed to normal tissue surrounding the wound. The flexible overlay, however, may be used within the perimeter of a wound in many cases because there is not typically a need to seal the flexible overlay to normal tissue surrounding the wound. Further, because there is typically no need for an adhesive seal, removal of the flexible overlay merely requires removal of the reduced pressure from the area under the flexible overlay. It is thus simple to remove from the patient. For this reason, it will tend to reduce the time required of medical staff for wound treatment, which will also tend to reduce the cost of wound treatment. In addition, there is no pain and discomfort for the patient when the flexible overlay is removed. Even if a limited amount of supplemental sealing means (such as an adhesive) are required to provide a seal at a portion of the flexible overlay that is adjacent to the surface surrounding the wound, the reduced amount of supplemental sealing means will cause a corresponding reduction in the amount of such pain and discomfort. Further, the preferred embodiments of the collapsed flexible overlay will have folds in its surface while in the collapsed state, so that fluid aspirated by the wound may flow along the folds to be removed from under the flexible overlay. In addition, if reduced pressure is lost under the flexible overlay, the flexible overlay will expand outward from the wound, providing a visual indication that reduced pressure has been lost. Finally, in its preferred embodiments, the flexible overlay is relatively inexpensive to manufacture, even though it meets the described needs.

In a first aspect of a second version of the present invention, the wound treatment appliance is comprised of a fluid impermeable flexible overlay, a collection chamber to receive and hold fluid aspirated from the wound, collection chamber attachment means to operably attach the collection chamber to the flexible overlay, as described in more detail below, and a reduced pressure supply means, which are described in more detail below. In this first aspect of the second version of the invention, the flexible overlay is adapted to be placed over and enclose all or a portion of the wound. In the various embodiments of this first aspect of the second version of the invention, except as described in more detail below, the flexible overlay has substantially the same structure, features characteristics and operation as the flexible overlay described above in connection with the first aspect of the first version of the invention. In addition, in this first aspect of the second version of the invention, the reduced pressure supply means is used to operably connect the collection chamber to a reduced pressure supply source that provides a supply of reduced pressure to the collection chamber, so that the volume within the collection chamber and under the impermeable overlay in the area of the wound to be treated are supplied with reduced pressure by the reduced pressure supply source. In the various embodiments of this second version of the invention, except as described in more detail below, the reduced pressure supply means to connect the reduced pressure supply source to the collection chamber in the embodiments of this second version of the invention may have substantially the same structure, features, characteristics and operation as the reduced pressure supply means described above in connection with the first version of the invention.

In this first aspect of the second version of the invention, the flexible overlay is attached by collection chamber attachment means to a collection chamber that receives and holds fluid aspirated from the wound. In some embodiments, the collection chamber may be approximately cylindrical in shape. In the various embodiments of this first aspect of the second version of the invention, the collection chamber attachment means operably attaches the collection chamber to the flexible overlay in a manner so that the fluid and reduced pressure are permitted to flow between the collection chamber and the volume under the flexible overlay in the area of the wound. In some embodiments of this first aspect of the second version of the invention, the collection chamber is positioned approximately adjacent to the impermeable flexible overlay on the side of the impermeable flexible overlay opposite the wound and the collection chamber attachment means is a rigid or semi-rigid connecting member positioned between the collection chamber and the impermeable flexible overlay. In these embodiments, the connecting member has a port therein that extends between the collection chamber and the flexible overlay. In embodiments where the flexible overlay is approximately elongated-conically shaped, the collection chamber and the collection chamber attachment means may be positioned approximately at the apex of the flexible overlay on the side of the impermeable flexible overlay opposite the wound. In some embodiments, the collection chamber may be approximately cylindrical in shape. In other embodiments, the collection chamber attachment means may be further comprised of a flow control means, which is described in more detail below, operably positioned between the collection chamber and the flexible overlay. In these embodiments, the flow control means permit the fluid to flow from the volume under the flexible overlay in the area of the wound into the collection chamber, but not in the opposite direction. In some of these embodiments, the flow control means may be comprised of a valve. In some of these embodiments, the valve may be comprised of a flapper-type valve. In yet other embodiments, the collection chamber is positioned approximately adjacent to the impermeable flexible overlay on the side of the impermeable flexible overlay opposite the wound and the collection chamber attachment means is comprised of a membrane. In these embodiments, the membrane acts as a barrier separating the collection chamber and the impermeable flexible overlay, so that the membrane acts as a portion of the surface of the collection chamber and a portion of the surface of the impermeable flexible overlay. In addition, the membrane has at least one port therein so that the volume within the collection chamber is in fluid communication with the volume under the impermeable flexible overlay in the area of the wound. In embodiments where the impermeable flexible overlay has an approximately conical shape or approximately elongated conical shape, the impermeable flexible overlay may have a base end opening and a top end opening opposite the base end opening. In these embodiments, the base end opening may have an either approximately circular shape or approximately elliptical shape sized to be placed over and enclose the area of the wound to be treated. The top end opening may have either an approximately circular shape or approximately elliptical shape. In these embodiments, the membrane is sized to be of the same shape and size as the top end opening and the membrane is positioned so that it is attached to the entire perimeter of the top end opening and covers the entire top end opening. In some embodiments, the collection chamber may have an approximately conical shape or approximately elongated conical shape with a chamber bottom end opening and a reduced pressure supply port positioned at the apex of the collection chamber opposite the chamber bottom end opening. In various embodiments, the chamber bottom end opening may have an either approximately circular shape or approximately elliptical shape adapted to be of approximately the same size and shape as the top end opening of the impermeable flexible overlay. In some of these embodiments, the perimeter of the chamber bottom end opening is attached to the membrane in a manner so that the collection chamber is airtight, except for the port in the membrane and the reduced pressure supply port. The reduced pressure supply port operably connects the reduced pressure supply means to the collection chamber. In some embodiments, the collection chamber attachment means is further comprised of flow control means operably connected with the at least one port, wherein the flow control means permits fluid aspirated from the wound to flow from the volume under the impermeable flexible overlay in the area of the wound through the at least one port to the collection chamber, but not in the opposite direction. In some of these embodiments, the flow control means is comprised of a valve. Preferably, this valve is comprised of a flapper-type valve.

In a second aspect of the second version of the present invention, the wound treatment appliance is comprised of a wound treatment device and a vacuum system, which is further comprised of a reduced pressure supply source that provides a supply of reduced pressure and reduced pressure supply means to operably connect the wound treatment device to the reduced pressure supply source. In various embodiments of this second aspect of the second version of the invention, except as described below, the wound treatment device and the reduced pressure supply means may generally have substantially the same structure, features, characteristics and operations as the appliance described above in connection with the first aspect of the second version of the invention. In these embodiments, the reduced pressure supply means operably connect the wound treatment device to the reduced pressure supply source so that the volume within the collection chamber and under the wound treatment device in the area of the wound is supplied with reduced pressure by the reduced pressure supply source.

In some embodiments of this second aspect of the second version of the invention, the reduced pressure supply source is comprised of a vacuum pump. In some of these embodiments, the reduced pressure supply source further comprises a control system for the vacuum pump, wherein the control system controls the operation of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms aspirated from the wound or fluids aspirated from the wound or both. In yet other embodiments, the vacuum pump is comprised of a portable vacuum pump. In still other embodiments, the reduced pressure supply means is comprised of flexible tubing. In other embodiments of this second aspect of the second version of the invention, the reduced pressure under the flexible overlay in the area of the wound is in the range from approximately 20 mm of Hg below atmospheric pressure to approximately 125 mm of Hg below atmospheric pressure. In yet other embodiments, the reduced pressure is applied in a cyclic nature, the cyclic nature providing alternating time periods of application of reduced pressure and without application of reduced pressure. In some embodiments of this second aspect of the second version of the invention, the wound treatment appliance further comprises tissue protection means, which are described in more detail below, to protect and strengthen the body tissue that is adjacent to the flexible overlay at the wound site. In some of these embodiments, the tissue protection means is a hydrocolloid material. In still other embodiments, wound packing means, which are described in more detail herein, are positioned between the wound treatment device and the portion of the wound to be treated.

A third aspect of the second version of the present invention discloses a method of treating a wound on a body. In one embodiment of this third aspect of the second version of the invention, the method comprises the following steps. First, a wound treatment device is positioned on the body over the area of the wound to be treated, wherein the wound treatment device is comprised of an impermeable flexible overlay, a collection chamber, and collection chamber attachment means, which are described in more detail below. In this embodiment, the flexible overlay is sized to be placed over and enclose the area of the wound to be treated and adapted to maintain reduced pressure in the area of the wound to be treated. In addition, in this embodiment, the collection chamber receives and holds fluid aspirated from the wound and the collection chamber attachment means, which is described in more detail below, operably attaches the collection chamber to the impermeable flexible overlay in a manner so that reduced pressure and the fluid are permitted to flow between the collection chamber and the impermeable flexible overlay. Second, the collection chamber is operably connected with a vacuum system for producing reduced pressure in the volume within the collection chamber and in the volume under the flexible overlay in the area of the wound to be treated. Third, the flexible overlay is collapsed in the approximate direction of the wound when reduced pressure is supplied to the volume under the flexible overlay in the area of the wound so that an approximately hermetic seal (described in more detail herein) is formed between the impermeable flexible overlay and the body in the area of the wound. Fourth, reduced pressure is maintained until the area of the wound being treated has progressed toward a selected stage of healing. In other embodiments of this third aspect of the first version of the invention, the method further comprises the step of placing tissue protection means on the tissue of the body that is to be approximately adjacent to the impermeable flexible overlay, such step being performed prior to positioning the impermeable flexible overlay over the area of the wound to be treated. The tissue protection means, which is described in more detail below, protects and strengthens the tissue of the body adjacent to the flexible overlay at the wound site. In yet other embodiments of this third aspect of the first version of the invention, the method further comprises the step of placing wound packing means (described in more detail herein) between the wound and the impermeable flexible overlay in the area of the wound to be treated, such step being performed prior to positioning the impermeable flexible overlay over the area of the wound to be treated. In still other embodiments of this third aspect of the first version of the invention, the reduced pressure under the impermeable overlay in the area of the wound is in the range from approximately 20 mm of Hg below atmospheric pressure to approximately 125 mm of Hg below atmospheric pressure. In still other embodiments of this third aspect of the first version of the invention, the reduced pressure is applied in a cyclic nature, the cyclic nature providing alternating time periods of application of reduced pressure and without application of reduced pressure.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 2A is a view of an embodiment of a wound treatment appliance of the first version of the present invention, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay;

FIG. 4 is a view of an embodiment of a wound treatment appliance of the first version of the present invention, in which an embodiment of an impermeable flexible overlay, shown in cross-sectional elevational view from the side of the flexible overlay, covers a wound, and in which an embodiment of a vacuum system, shown in perspective view from the side of and below the vacuum system, provides reduced pressure within the area under the flexible overlay; and FIG. 5 is a view of an embodiment of a wound treatment appliance of a second version of the present invention, in which an embodiment of an impermeable flexible overlay, shown in perspective view from the side of and above the flexible overlay, covers a wound, and in which an embodiment of a vacuum system, depicted generally and shown in schematic elevation view, provides reduced pressure within the area under the flexible overlay.

DETAILED DESCRIPTION OF THE PREFERRED EMBODIMENTS

Figure 1A:
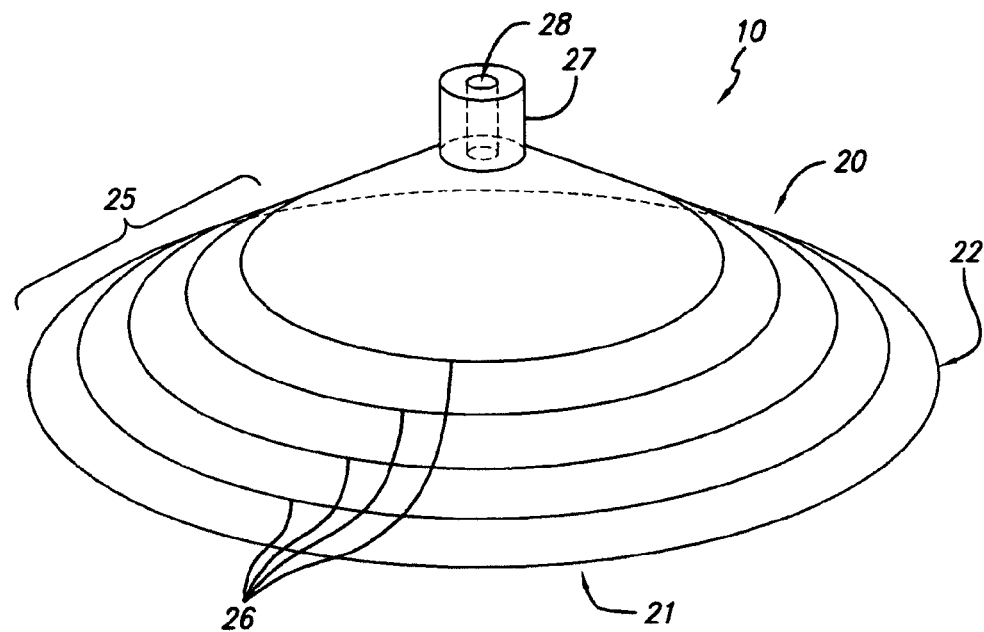
FIG. 1A is a perspective view of an embodiment of an impermeable flexible overlay of a wound treatment appliance of a first version of the present invention, as viewed from the side of and above the flexible overlay comprising the wound treatment appliance (as the flexible overlay would be oriented when placed on the body of a patient)
Figure 1B:
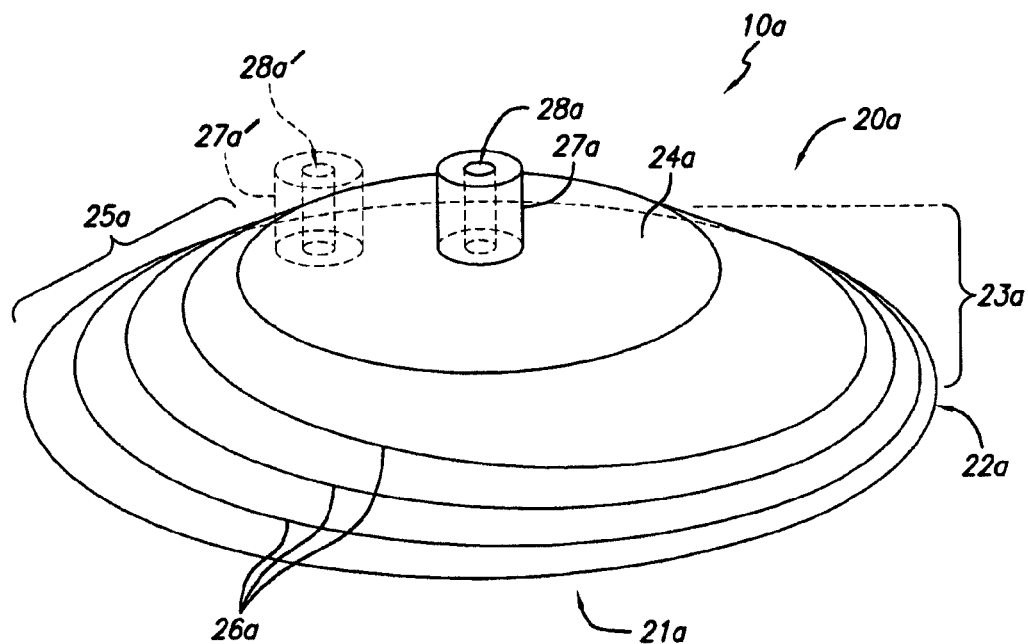
FIG. 1B is a perspective view of another embodiment of an impermeable flexible overlay of a wound treatment appliance of the first version of the present invention, as viewed from the side of and above the flexible overlay comprising the wound treatment appliance (as the flexible overlay would be oriented when placed on the body of a patient)
Figure 1C:
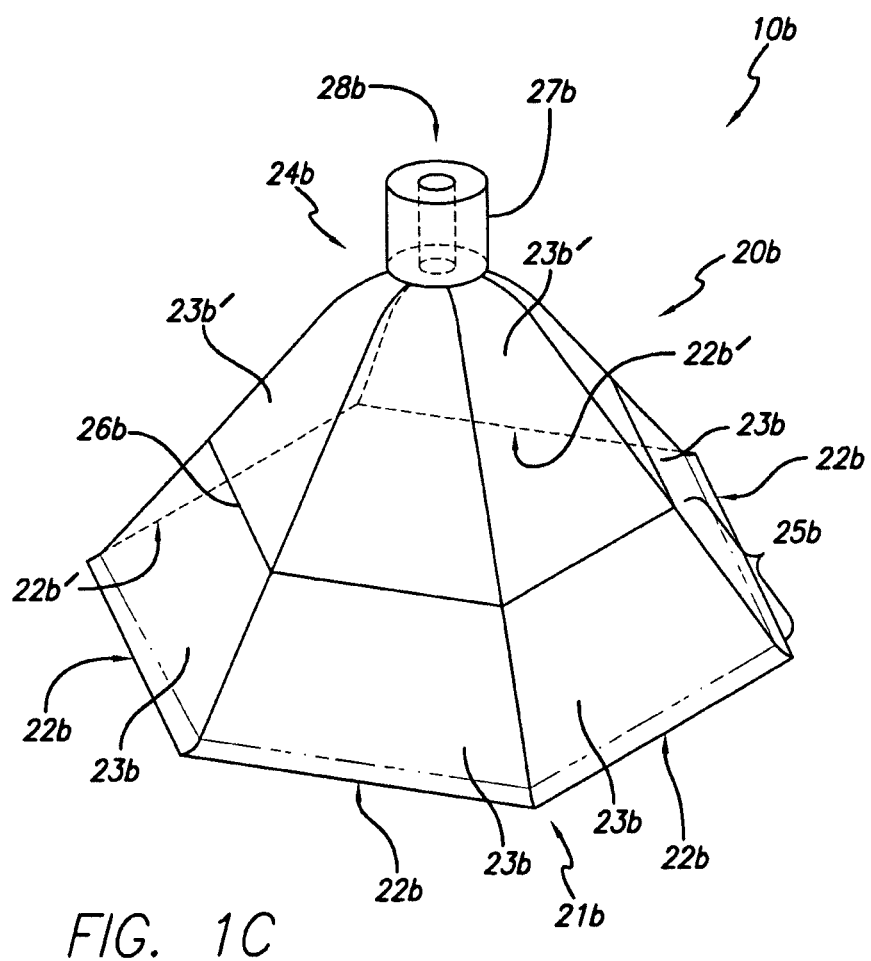
FIG. 1C is a perspective view of another embodiment of an impermeable flexible overlay of a wound treatment appliance of the first version of the present invention, as viewed from the side of and above the flexible overlay comprising the wound treatment appliance (as the flexible overlay would be oriented when placed on the body of a patient)

In accordance with the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. One embodiment of a first aspect of a first version of the invention is a wound treatment appliance 10 that is comprised of the fluid impermeable flexible overlay 20 illustrated in FIG. 1A and reduced pressure supply means, which are described in more detail below. In this embodiment, the flexible overlay 20 has an approximately elongated conical shape, having an opening 21 with an opening perimeter 22 adjacent to the opening 21 (at the base of the elongated conical shape) that is approximately elliptical in shape. The flexible overlay 20 illustrated in FIG. 1A is in its natural shape, as it exists prior to being applied to a patient for treatment of all or a portion of a wound. In other embodiments, the flexible overlay 20 may have other shapes. For example, the flexible overlay 20 may be approximately conical in shape, rather than the approximately elongated conical shape illustrated in FIG. 1A. As another example, as illustrated in FIG. 1B, only the bottom portion 23a of the flexible overlay 20a may have an approximately elongated conical shape. In this embodiment, and in the same manner as illustrated in FIG. 1A, the bottom portion 23a has an opening 21a with an opening perimeter 22a adjacent to the opening 21a (at the base of the elongated conical shape) that is approximately elliptical in shape. In the embodiment of the flexible overlay illustrated in FIG. 1B, the top portion 24a is flatter than the comparable portion of the flexible overlay 20 in the embodiment illustrated in FIG. 1A. In other embodiments, the top portion 24a of the flexible overlay 20a may have almost any shape that is adaptable to a bottom portion 23a having an approximately elongated conical shape. In addition, in yet other embodiments of this first aspect of the first version of the invention, the bottom portion 23a of the flexible overlay 20a may be in the approximate shape of a cone, rather than the elongated conical shape illustrated in FIG. 1B. In yet another embodiment, as illustrated in FIG. 1C, the flexible overlay 20b is comprised of six cover portions 23b, 23b', where the cover portions 23b are viewable in FIG. 1C and the cover portions 23b' are illustrated by phantom lines. In this embodiment, each of such cover portions 23b, 23b' is approximately triangular in shape, and one point of each of the at least three cover portions 23b, 23b' is joined to form an apex 24b of the impermeable flexible overlay 20b. One side of each cover portion 23b, 23b' adjacent to the apex 24b is joined to an adjacent side of another of such cover portions 23b, 23b' so that the bases 22b, 22b' of the cover portions 23b, 23b', respectively, form an opening 21b sized to be placed over and enclose the area of the wound to be treated. In other embodiments, the flexible overlay 20b may have a different number of cover portions 23b, 23b'. Preferably, in these embodiments, there are at least three cover portions 23b, 23b'. In addition, in yet other embodiments, the flexible overlay 20b may have cover portions 23b, 23b' having a different shape, such as trapezoidal or parabolic. In still other embodiments, the flexible overlay 20, 20a, 20b may be of almost any shape that may be adaptable for treating all or a portion of a wound, as long as the flexible overlay 20, 20a, 20b is flexible, as described in more detail below, and the interior surface of the flexible overlay 20, 20a, 20b is adapted to make an approximately hermetic seal with the body of the patient at the site of the wound, as described in more detail below. Referring again to FIG. 1A as an example, in some embodiments of this first aspect of the first version of the invention, the interior surface of the flexible overlay 20 is adapted to make an approximately hermetic seal with the body of the patient at the site of the wound by having a surface area larger than the surface area of the portion of the body of the patient covered by the flexible overlay 20, as described in more detail below.

The preferred shape and size of the flexible overlay 20, 20a, 20b is dependent upon the size of the portion of the wound to be treated, the shape and contour of the portion of the body that is to be covered by the flexible overlay 20, 20a, 20b at the site of the wound, the magnitude of the reduced pressure to be maintained under the flexible overlay 20, 20a, 20b. More preferred, as illustrated in FIG. 1B, the flexible overlay 20a has an approximately elongated conically shaped bottom portion 23a. Most preferred, as illustrated in FIG. 1A, the flexible overlay 20 is shaped approximately as an elongated cone. The preferred thickness of the portion 25, 25a, 25b of the flexible overlay 20, 20a, 20b adjacent to the open end 21, 21a, 21b of the flexible overlay 20, 20a, 20b is dependent upon the size and shape of the flexible overlay 20, 20a, 20b, the shape and contour of the portion of the body that is to be covered by the flexible overlay 20, 20a, 20b at the site of the wound, the magnitude of the reduced pressure to be maintained under the flexible overlay 20, 20a, 20b, and other factors, such as the depth of the wound and the amount of the desired collapse of the flexible overlay 20, 20a, 20b. For example, in the embodiment illustrated in FIG. 1A, for a flexible overlay 20 constructed of silicone and having an approximately elongated conical shape with an opening 21 having a major diameter of approximately 7 inches and a minor diameter of approximately 4 inches, the preferred thickness of the portion 25 of the flexible overlay 20 adjacent to the open end 21 of the flexible overlay 20 is in the range from ($1/32$) inches to ($3/32$) inches. More preferred in this embodiment, the thickness of the portion 25 of the flexible overlay 20 adjacent to the open end 21 of the flexible overlay 20 is approximately ($1/16$) inches. It is to be noted that in other embodiments the thickness of the flexible overlay 20, including the portion 25 of the flexible overlay 20 adjacent to the open end 21 of the flexible overlay 20, may vary from location to location on the flexible overlay 20.

In the embodiment of the flexible overlay 20 illustrated in FIG. 1A, the flexible overlay 20 has a series of raised beads 26 on the outside surface of the flexible overlay 20. In this embodiment, the raised beads 26 are generally parallel to the perimeter 22 of the opening 21 of the flexible overlay 20. The same is also true of the raised bead 26b of the flexible overlay 20b of the embodiment illustrated in FIG. 1C. In other embodiments, such as that illustrated in FIG. 1B, the raised beads 26a may have a different orientation. In still other embodiments, the raised beads 26, 26a, 26b may be in almost any orientation desired by the user of the wound treatment appliance 10, 10a, 10b. In various embodiments of this first aspect of the first version of the invention, as illustrated in FIG. 1A, the raised beads 26 may provide a guide for the user administering the reduced pressure treatment to cut away a portion of the flexible overlay 20, so that the perimeter 22 of the opening 21 of the flexible overlay 20 is smaller than it was originally. For example, by cutting along the parallel raised beads 26 of the flexible overlay 20 of FIG. 1A, the size of the opening 21 of the flexible overlay 20 can be made smaller while the shape of the perimeter 22 remains approximately the same. It is to noted, however, that in various embodiments of this first aspect of the first version of the invention, as described in more detail below, the flexible overlay 20 may be cut into different shapes in order to adapt the flexible overlay 20 for use with different shapes and contours of the surface of the body at the site of the wound.

In the various embodiments of this first aspect of the first version of the invention, the flexible overlay 20, 20a, 20b may be comprised of almost any medical grade flexible material that is currently known in the art or that may be developed in the art in the future, as long as such material is fluid-impermeable, suitable for purposes of wound treatment (e.g., can be sterilized and does not absorb significant amounts of wound exudate), and is capable of forming an approximately hermetic seal with the surface of the body at the site of the wound, as described in more detail below. For example, the flexible overlay 20, 20a, 20b may be comprised of rubber (including neoprene), and flexible polymer materials, such as silicone, silicone blends, silicone substitutes, polyester, vinyl, polyimide, polyethylene napthalate, polycarbonates, polyester-polycarbonate blends, or a similar polymer, or combinations of all such materials. Preferably, the flexible overlay 20, 20a, 20b is comprised of silicone. Although the raised beads 26, 26a, 26b may be constructed of a material different from the material comprising the remainder of the flexible overlay 20, 20a, 20b in various embodiments of the invention, the raised beads 26, 26a, 26b are preferably constructed from the same material comprising the remainder of the flexible overlay 20, 20a, 20b. In other embodiments, the raised beads 26, 26a, 26b may be placed on the flexible overlay 20, 20a, 20b by means of a mark, such as indelible ink, on the surface of the flexible overlay 20, 20a, 20b. It is to be noted that in various embodiments of this first aspect of the first version of the invention, the flexible overlay 20, 20a, 20b may be constructed in whole or in part of gas-permeable materials, allowing limited amounts of oxygen to penetrate the flexible overlay 20, 20a, 20b so that the area of the wound under the flexible overlay 20, 20a can "breathe." It is also to be noted that all portions of the flexible overlay 20, 20a, 20b are preferably constructed of one type of polymer material, such as silicone. The flexible overlay 20, 20a, 20b may be constructed using any suitable means currently known in the art or that may be developed in the art in the future. For example, a flexible overlay 20, 20a, 20b constructed of silicone may be manufactured by means of injection molding.

In the embodiments of the flexible overlay 20, 20a, 20b illustrated in FIG. 1A, FIG. 1B, and FIG. 1C, respectively, each of the flexible overlays 20, 20a, 20b further comprises a port 27, 27a, 27b adapted to receive a reduced pressure supply means to supply reduced pressure to the area of the wound under the flexible overlay 20, 20a, 20b. Although the port 27 is positioned at approximately the apex of the elongated cone-shaped flexible overlay 20 in the embodiment illustrated in FIG. 1A, and the port 27b is positioned at approximately the apex 24b of the triangular-shaped cover portions 23b, 23b' in the embodiment illustrated in FIG. 1C, which is the preferred location, the port may be located at another location on the flexible overlay in other embodiments. In such embodiments, and referring to FIG. 1B as an example, the port 27a (and alternate port 27a') may be located at almost any location on the surface of the flexible overlay 20a as long as the port 27a, 27a' does not adversely affect the ability of the flexible overlay 20a to make an approximately hermetic seal with the surface of the body at the wound site, as described in more detail below. For example, the port 27a, 27a' may not be located too close to the perimeter 22a of the opening 21a of the flexible overlay 20a because the approximately hermetic seal with the surface of the body is typically formed at that location. In the embodiment of the flexible overlay 20a illustrated in FIG. 1B, the alternate port 27a' may preferably be located at any location on the top portion 24a of the flexible overlay 20a, and more preferably, the port 27a is located at the center of the top portion 24a of the flexible overlay 20a. Referring again to FIG. 1A as an example, although the port 27 may be constructed of a material different from the material comprising the remainder of the flexible overlay 20 in various embodiments of the invention, the port 27 is preferably constructed from the same material comprising the remainder of the flexible overlay 20. In the embodiments of the flexible overlay 20, 20a, 20b illustrated in FIG. 1A, FIG. 1B, and FIG. 1C, respectively, the ports 27, 27a, 27b are generally cylindrical in shape and are further comprised of an approximately cylindrical channel 28, 28a, 28b, respectively, that extends from the top of each of the ports 27, 27a, 27b, respectively, to the bottom of the ports 27, 27a, 27b, respectively. The ports 27, 27a, 27b of these embodiments are thus able to receive a vacuum system or reduced pressure supply means, which are described in more detail below, adapted to be connected to this shape of port 27, 27a, 27b, respectively, and channel 28, 28a, 28b, respectively. In other embodiments of this first aspect of the first aspect of the first version of the invention, the ports 27, 27a, 27b or the channels 28, 28a, 28b, respectively, or both may have different shapes and configurations as may be desired to adapt and connect the ports 27, 27a, 27b, respectively, and the channels 28, 28a, 28b, respectively, to the vacuum system or reduced pressure supply means, which are described in more detail below.

An embodiment of a second aspect of the first version of the present invention is the wound treatment appliance 110 illustrated in FIG. 2A. In this embodiment, the wound treatment appliance 110 is comprised of a wound treatment device 115 and a vacuum system, generally designated 150, that is operably connected to, and provides a supply of reduced pressure to, the wound treatment device 115. Also in this embodiment, the wound treatment device 115 is comprised of a flexible overlay 120. In addition, in this embodiment, the vacuum system 150 is further comprised of a reduced pressure supply source, generally designated 130, which is illustrated schematically and described in more detail below, and reduced pressure supply means, generally designated 140, which are illustrated schematically and described in more detail below. Also in this embodiment, the reduced pressure supply means 140 are used to connect the reduced pressure supply source 130 to the flexible overlay 120 in a manner so that reduced pressure is supplied to the volume under the flexible overlay 120 in the area of the wound 160, as described in more detail below. In the embodiment of the second aspect of the first version of the invention illustrated in FIG. 2A, the flexible overlay 120 has substantially the same structure, features, characteristics and operation as the flexible overlay 20 described above and illustrated in connection with FIG. 1A. It is to be noted, however, that in other embodiments of this second aspect of the first version of the invention, the flexible overlay 120 may have substantially the same structure, features and characteristics as any embodiment of all of the flexible overlays 20, 20a, 20b of the first aspect of the first version of the invention described above and illustrated in connection with FIG. 1A, FIG. 1B, and FIG. 1C. FIG. 2A also illustrates an example of how the embodiment of the flexible overlay 20 illustrated in FIG. 1A may be used to provide reduced pressure treatment for a wound 160 on the body 170 of a patient. In this example, the flexible overlay 120 is placed over and encloses the entire wound 160, as described in more detail below. In other embodiments, the flexible overlay 120 need not enclose the entire wound 160.

In the embodiment illustrated in FIG. 2A, the reduced pressure supply source 130 of the vacuum system 150, which produces a source of reduced pressure or suction that is supplied to the flexible overlay 120, is comprised of a vacuum pump 131, a control device 132, and a filter 133. Although the preferred means of producing the reduced pressure or suction is a vacuum pump 131 in this embodiment, in other embodiments of this second aspect of the first version of the invention other means may be used, such as an outlet port of a centralized hospital vacuum system. In the illustrated embodiment, predetermined amounts of suction or reduced pressure are produced by the vacuum pump 131. The vacuum pump 131 is preferably controlled by a control device 132, such as a switch or a timer that may be set to provide cyclic on/off operation of the vacuum pump 131 according to user-selected intervals. Alternatively, the vacuum pump 131 may be operated continuously without the use of a cyclical timer. In addition, in some embodiments the control device 132 may provide for separate control of the level of reduced pressure applied to the wound 160 and the flow rate of fluid aspirated from the wound 160. In these embodiments, relatively low levels of reduced pressure may be maintained in the area of the wound 160 under the wound treatment device 115, while still providing for the removal of a relatively large volume of exudate from the wound 160. A filter 133, such as a micropore filter, is preferably attached to the inlet of the vacuum pump 131 to prevent potentially pathogenic microbes or aerosols from contaminating, and then being vented to atmosphere by, the vacuum pump 131. In other embodiments, the filter 133 may also be a hydrophobic filter that prevents any exudate from the wound from contaminating, and then being vented to atmosphere by, the vacuum pump 131. It is to be noted that in other embodiments of the invention, the reduced pressure supply source 130 may not have a filter 133 or a control 132 or any combination of the same.

In the embodiment of the second aspect of the first version of the invention illustrated in FIG. 2A, the reduced pressure supply means 140 of the vacuum system 150, which are used to connect the reduced pressure supply source 130 to the flexible overlay 120 so that reduced pressure is supplied to the volume under the flexible overlay 120 in the area of the wound 160 is comprised of at least one tubing member 141. In this embodiment, the at least one tubing member 141 is sufficiently flexible to permit movement of the at least one tubing member 141, but is sufficiently rigid to resist constriction when reduced pressure is supplied to the flexible overlay 120 or when the location of the wound 160 is such that the patient must sit or lie upon the at least one tubing member 141 or upon the wound treatment device 115. In the embodiment illustrated in FIG. 2A, the at least one tubing member 141 is connected to the flexible overlay 120 by inserting one end of the at least one tubing member 141 into the opening 128 of the port 127 of the flexible overlay 120. In this embodiment, the at least one tubing member is held in place in the opening 128 by means of an adhesive. It is to be noted that in other embodiments of this second aspect of the first version of the invention, the at least one tubing member 141 may be connected to the port 127 of the flexible overlay 120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 127 and the at least one tubing member 141 may be fabricated as a single piece. Similar means may be used to connect the other end of the at least one tubing member 141 to the vacuum pump 131 or other reduced pressure supply source 130 providing the reduced pressure.

Figure 2B:
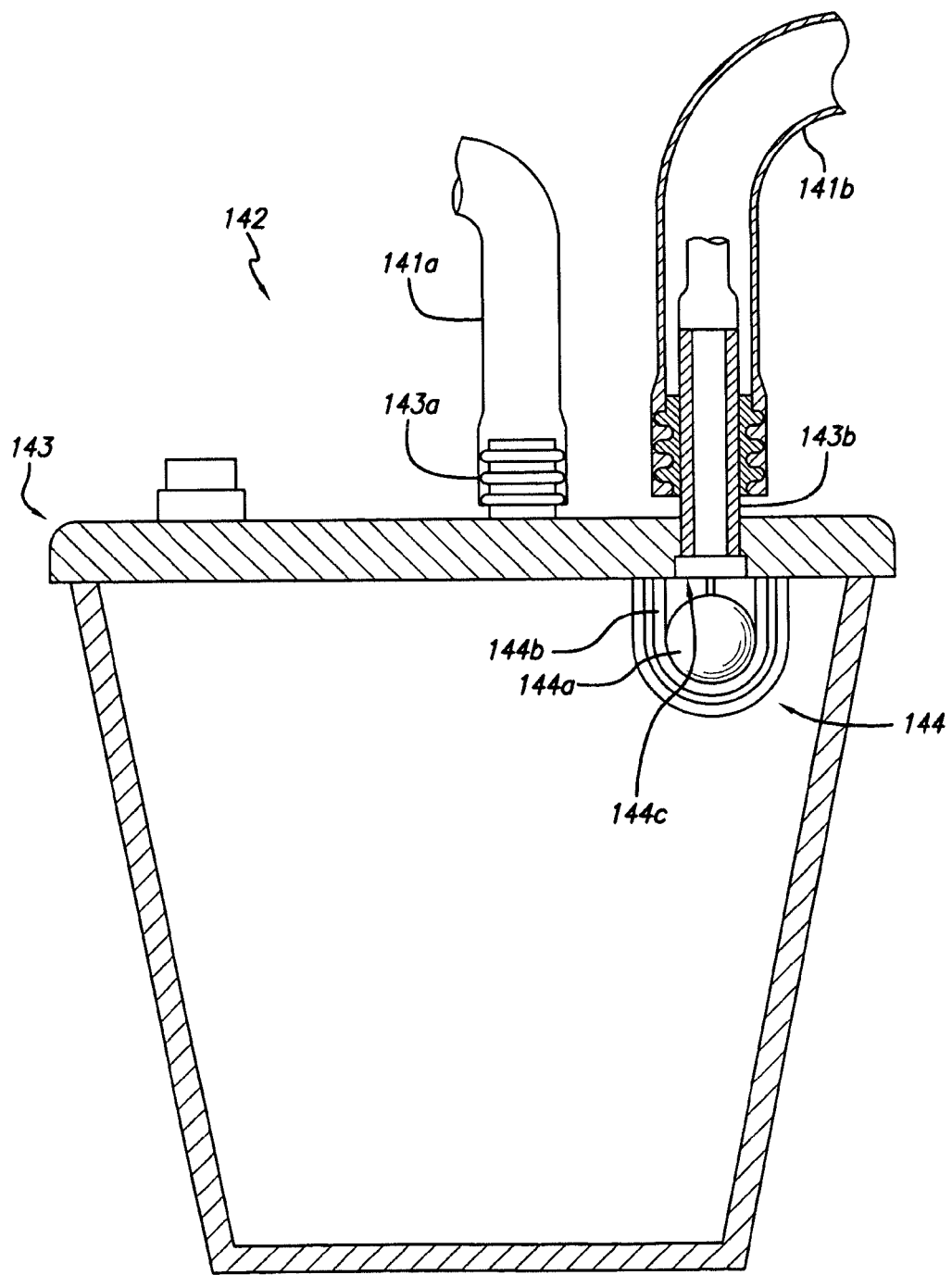
FIG. 2B is a sectional elevational detailed view of an embodiment of a collection container and the shutoff mechanism portion of the collection system of FIG. 2A.

In the embodiment illustrated in FIG. 2A, the reduced pressure supply means 140 further comprises a fluid collection system, generally designated 142, that is interconnected between the suction pump 131 and the flexible overlay 120 to remove and collect any exudate that may be aspirated from the wound 160 and collected by the flexible overlay 120. The flexible overlay 120 functions to actively draw fluid or exudate from the wound 160. Collection of exudate in a fluid collection system 142 intermediate the pump 131 and the flexible overlay 120 is desirable to prevent clogging of the pump 131. The fluid collection system 142 is comprised of a fluid-impermeable collection container 143 and a shutoff mechanism 144, which are described in more detail below in connection with FIG. 2B. The container 143 may be of any size and shape capable of intercepting and retaining a predetermined amount of exudate. Many examples of such containers are available in the relevant art. Referring to FIG. 2B, which is an enlarged elevational cross-sectional view of the preferred embodiment of the container 143, the container 143 includes a first port 143a at the top opening of the container 143 for sealed connection to tubing member 141a, where the other end of the tubing member 141a is connected to the flexible overlay 120. The first port 143a enables suction to be applied to the flexible overlay 120 through the tubing 141a and also enables exudate from the portion of the wound 160 covered by the flexible overlay 120 to be drained into the container 143. The container 143 provides a means for containing and temporarily storing the collected exudate. A second port 143b is also provided on the top of the container 143 to enable the application of suction from the vacuum pump 131. The second port 143b of the collection system 142 is connected to the vacuum pump 131 by tubing member 141b. The collection system 142 is sealed generally gas-tight to enable the suction pump 131 to supply suction to the flexible overlay 120 through the collection system 142.

The embodiment of the collection system 142 illustrated in FIG. 2B also includes a shutoff mechanism for halting or inhibiting the supply of the reduced pressure to the flexible overlay 120 in the event that the exudate aspirated from the wound 160 exceeds a predetermined quantity. Interrupting the application of suction to the flexible overlay 120 is desirable to prevent exsanguination in the unlikely event a blood vessel ruptures under the flexible overlay 120 during treatment. If, for example, a blood vessel ruptures in the vicinity of the wound 160, a shut-off mechanism would be useful to prevent the vacuum system 150 from aspirating any significant quantity of blood from the patient. In the preferred embodiment of the shutoff mechanism 144, as illustrated in FIG. 2B, the shutoff mechanism 144 is a float valve assembly in the form of a ball 144a which is held and suspended within a cage 144b positioned below a valve seat 144c disposed within the opening at the top of the container below the second port 143b that will float upon the exudate and will be lifted against the valve seat 144c as the container 143 fills with exudate. When the ball 144a is firmly seated against the valve seat 144c, the float valve blocks the second port 143b and thereby shuts off the source of suction from the vacuum system 150. In other embodiments of the container 143, other types of mechanisms may also be employed to detect the liquid level within the container 143 in order to arrest operation of the vacuum system 50. In addition, in various embodiments of this second version of the invention, the shutoff mechanism 144 may be comprised of any means that enables the vacuum system 150 to halt the supply of reduced pressure to the flexible overlay 120 at any time that the volume of exudate from the wound 160 exceeds a predetermined amount. Such means may include mechanical switches, electrical switches operably connected to the vacuum system controller 132, optical, thermal or weight sensors operably connected to the vacuum system controller 132, and any other means that are currently known in the relevant art or that may be developed in the art in the future.

In some embodiments of this second version of the invention, the wound treatment appliance 110 further comprises tissue protection means 175 to protect and strengthen the body tissue 171 that is adjacent to the flexible overlay 120 at the wound site 161. The tissue protection means 175 protects the tissue 171 by preventing abrasion and maceration of the tissue. Preferably, the tissue protection means 175 is a hydrocolloid material, such as COLOPAST Hydrocolloid 2655, anhydrous lanoline, or any combination of such hydrocolloid materials. More preferably, the tissue protection means 175 is COLOPAST Hydrocolloid 2655. The tissue protection means 175 may be applied to the body tissue 171 to be protected, or it may be applied to the surface of the flexible overlay 120 that is to be in contact with the body tissue 171, or both, prior to placing the flexible overlay 120 on the surface of the body 170 at the wound site 161. It is to be noted that application of the tissue protection means 175 to the body tissue 171 that is adjacent to the flexible overlay 120 at the wound site 161 may only entail application of the tissue protection means 175 to the portion of the body tissue 171 adjacent to the flexible overlay 120 that requires such protection.

FIG. 2A also illustrates an example of how the embodiment of the flexible overlay 20 illustrated in FIG. 1A (which is flexible overlay 120 in FIG. 2A) may be used to provide reduced pressure treatment for a wound 160 on the body 170 of a patient. In this example, the flexible overlay 120 is removed from an aseptic package in which it is stored. The flexible overlay 120 is then placed over and encloses the portion of the wound 160 to be treated, which is the entire wound 160 in this example. The flexible overlay 120 is also connected to the vacuum system 150 by means of the port 127 on the flexible overlay 120 either before, after or during the placement of the flexible overlay 120 over the wound 160. Where it is deemed necessary by the user of the wound treatment appliance 110, tissue protection means 175, as described above, may be placed on a portion of the flexible overlay 120, on the body tissue 171 to be protected, or both, prior to placing the flexible overlay 120 over the wound 160. In the example illustrated in FIG. 2A, the interior surface portions 129 of the flexible overlay 120 positioned around and adjacent to the perimeter 122 of the opening 121 of the flexible overlay 120 are at (or can be deformed to be at) a relatively acute angle relative to the surrounding surface of the body 170. Such deformation may be caused by the user of the wound treatment appliance 110 exerting mild pressure on the portions 129 of the flexible overlay 120 positioned around and adjacent to the perimeter 122 of the opening 121 of the flexible overlay 120 so that they are in contact with the surface of the body 170 surrounding the wound 160. Reduced pressure is then supplied to the flexible overlay 120 by the vacuum system 150. When reduced pressure is applied to the volume under the flexible overlay 120 in the area of the wound 160, the flexible overlay 120 is drawn downward by the reduced pressure, collapsing the flexible overlay 120 in the approximate direction of the wound 160. As the flexible overlay 120 collapses, the portions 129 of the flexible overlay 120 adjacent to the perimeter 122 of the opening 121 of the flexible overlay 120 are drawn tightly against the surface of the body 170 surrounding the wound 160, thus forming an approximately hermetic seal between the portions 129 of the flexible overlay 120 adjacent to the perimeter 122 of the opening 121 of the flexible overlay 120 and the portion of the body 170 adjacent to such portions 129. References to an "approximately hermetic seal" herein refer generally to a seal that may be made gas-tight and liquid-tight for purposes of the reduced pressure treatment of the wound 160. It is to be noted that this seal need not be entirely gas-tight and liquid-tight. For example, the approximately hermetic seal may allow for a relatively small degree of leakage, so that outside air may enter the volume under the flexible overlay 120 in the area of the wound 160, as long as the degree of leakage is small enough so that the vacuum system 150 can maintain the desired degree of reduced pressure in the volume under the flexible overlay 120 in the area of the wound 160. As another example, the approximately hermetic seal formed by the collapsing flexible overlay 120 may not be solely capable of maintaining the reduced pressure in the volume under the impermeable overlay 120 in the area of the wound 160 due to the shape of the body 170 at the site of the wound 160 or for other reasons. In these cases, it may be necessary to provide supplemental sealing means, which are used to provide a seal between the portions of the flexible overlay 120 and the body 170 where the approximately hermetic seal is not adequate to permit reduced pressure to be maintained in the volume under the flexible overlay 120 in the area of the wound 160. For example, in the illustrated embodiment, the supplemental sealing means 176 may be an adhesive applied to a portion of the impermeable overlay 120 or a portion of the body 170 in a manner similar to the application of the tissue protection means 175 described above. In other embodiments, the supplemental sealing means 176 may be comprised of almost any suitable means to provide an adequate seal. For example, the supplemental sealing means 176 may be comprised of an adhesive, an adhesive tape, a stretch fabric that covers the wound treatment device 115 and is wrapped around a portion of the body 170 of the patient in the area of the wound 160, lanoline, or any combination of such means. It is also to be noted that in this embodiment at least one fold 129a forms in the surface of the flexible overlay 120 when it collapses, so that fluids aspirated by the wound 160 flow along the at least one fold 129a to the port 127, where the fluid is removed from the flexible overlay 120 by means of the reduced pressure supply means 140 cooperating with the reduced pressure supply source 130. Thus, in the preferred embodiments, the impermeable overlay 120 is constructed of a material, and has a size, shape and thickness, that permits the flexible overlay 120 to collapse in the direction of the wound 160 and form an approximately hermetic seal with the body 170 when reduced pressure is applied to the volume under the flexible overlay 120 in the area of the wound 160, while still being rigid enough to support the approximately hermetic seal with the body 170 and to support the at least one fold 129a. It is also to be noted that the volume under the impermeable overlay 120 in the area of the wound 160 may be minimal while the impermeable overlay 120 is in its collapsed state over the wound 160. In the preferred embodiments of this second aspect of the first version of the invention, the reduced pressure maintained in the volume under the flexible overlay 120 in the area of the wound 160 is in the range from approximately 20 mm of Hg below atmospheric pressure to approximately 125 mm of Hg below atmospheric pressure. In yet other embodiments, the reduced pressure is applied to the flexible overlay 120 in a cyclic nature, the cyclic nature providing alternating time periods of application of reduced pressure and non-application of reduced pressure. In all of these embodiments, the reduced pressure is maintained in the volume under the flexible overlay 120 in the area of the wound 160 until the wound 160 has progressed toward a selected stage of healing.

Figure 3:
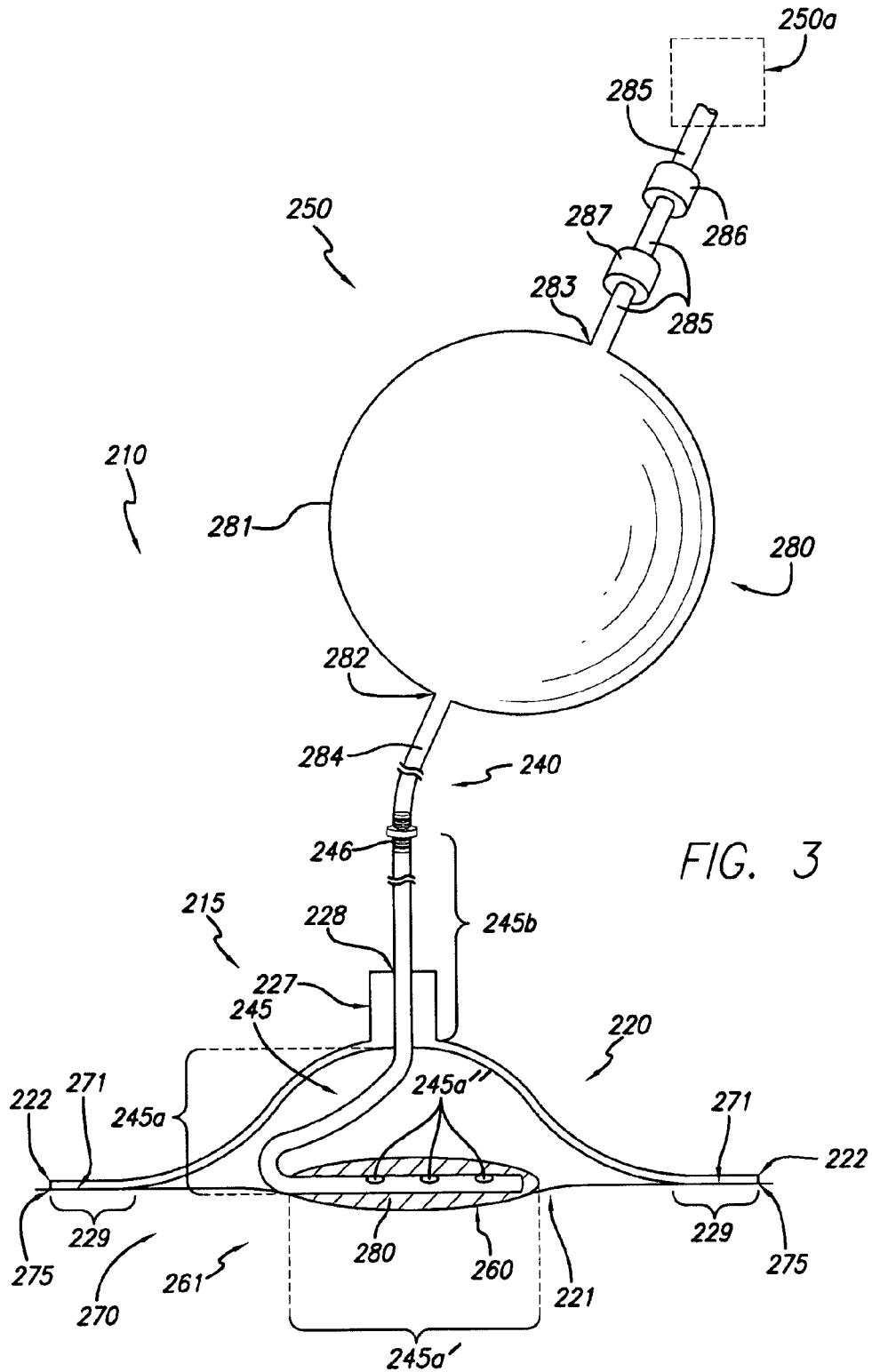
FIG. 3 is a view of an embodiment of a wound treatment appliance of the first version of the present invention, in which an embodiment of an impermeable flexible overlay, shown in cross-sectional elevational view from the side of the flexible overlay, covers a wound and wound packing means, and in which an embodiment of a vacuum system, shown in elevational view, provides reduced pressure within the area under the flexible overlay.

An embodiment of a third aspect of the first version of the invention is the wound treatment appliance 210 illustrated in FIG. 3. In this embodiment, the wound treatment appliance 210 is comprised of a wound treatment device 215 and a vacuum system, generally designated 250, that is operably connected to, and provides a supply of reduced pressure to, the wound treatment device 215. In addition, in this embodiment, the vacuum system 250 is further comprised of a reduced pressure supply source, generally designated 280, which is described in more detail below, and reduced pressure supply means, generally designated 240, which are described in more detail below. Also in this embodiment, the wound treatment device 215 is further comprised of an impermeable flexible overlay 220, wound packing means 278, and a suction drain 245. In the embodiment of the third aspect of the first version of the invention illustrated in FIG. 3, the flexible overlay 220 has substantially the same structure, features, characteristics and operation as the flexible overlay 20 described above and illustrated in connection with FIG. 1A. It is to be noted, however, that in other embodiments of this third aspect of the first version of the invention, the flexible overlay 220 may have substantially the same structure, features, characteristics and operation as any embodiment of all of the flexible overlays 20, 20a, 20b of the first aspect of the first version of the invention described above and illustrated in connection with FIG. 1A, FIG. 1B, and FIG. 1C, respectively. It is also to be noted that in other embodiments the wound treatment device 220 may be comprised of almost any type of flexible, semi-rigid, or rigid wound covering apparatus currently known in the relevant art or that may be developed in the relevant art in the future that has a port and is designed to cover and enclose a wound and maintain reduced pressure in the area of the wound under the wound covering apparatus. For example, the impermeable overlay 220 may generally have substantially the same structure, features and characteristics as the embodiments of the rigid, semi-rigid or flexible wound covers described in U.S. patent application Ser. No. 10/652,100, which was filed by the present inventor with the U.S. Patent and Trademark Office on Aug. 28, 2003, and U.S. patent application entitled "Improved Reduced Pressure Wound Treatment Appliance," which was filed by the present inventor with the U.S. Patent and Trademark Office on or about Dec. 30, 2004, the disclosures of which are incorporated herein by reference. In these embodiments, the impermeable overlay 220 may be sealed to the body in the area of the wound using any means disclosed in such applications or using the supplemental sealing means 176 described above and illustrated in connection with FIG. 2A. In the embodiment illustrated in FIG. 3, the flexible overlay 220 is placed over and encloses the entire wound 260 and is illustrated in a state of partial collapse, with the portion 229 of the flexible overlay 220 adjacent to the opening 221 in the perimeter 222 of the flexible overlay 220 forming an approximately hermetic seal with the adjacent portions 271 of the body 270. It is to be noted that in various embodiments of this third aspect of the first version of the invention, the wound treatment appliance 210 may also be comprised of tissue protection means 275, which may be substantially the same as the tissue protection means 175 of the second aspect of the first version of the invention described above and illustrated in connection with FIG. 2A.

In the embodiment of the third aspect of the first version of the invention illustrated in FIG. 3, the wound treatment device 215 is further comprised of wound packing means 278, which is placed in the area of the wound 260 under the flexible overlay 220. In this embodiment, the flexible overlay 220 is placed over the area of the wound 260 to be treated and the wound packing means 278 when the flexible overlay 220 is positioned on the surface of the body 270 at the site of the wound 260. In some embodiments of this third aspect of the first version of the invention, the wound packing means 278 may be placed within the wound 260 to prevent overgrowth of the tissue in the area of the wound 260. For example, and preferably in these cases, the wound packing means 278 may comprised of absorbent dressings, antiseptic dressings, non-adherent dressings, water dressings, or combinations of such dressings. More preferably, the wound packing means 278 may be comprised of gauze or cotton or any combination of gauze and cotton. In still other embodiments of this third aspect of the first version of the invention, the wound packing means 278 may be comprised of an absorbable matrix adapted to encourage growth of the tissue in the area of the wound 260 into the matrix. In these embodiments, the absorbable matrix (as wound packing means 278) is constructed of an absorbable material that is absorbed into the epithelial and subcutaneous tissue in the wound 260 as the wound 260 heals. The matrix (as wound packing means 278) may vary in thickness and rigidity, and it may be desirable to use a spongy absorbable material for the patient's comfort if the patient must lie upon the wound treatment device 215 during treatment. The matrix (as wound packing means 278) may also be perforated and constructed in a sponge-type or foam-type structure to enhance gas flow and to reduce the weight of the matrix. Because of the absorbable nature of the absorbable matrix (as wound packing means 278), the matrix should require less frequent changing than other dressing types during the treatment process. In other circumstances, the matrix (as wound packing means 278) may not need to be changed at all during the treatment process. In some embodiments of this third aspect of the first version of the invention, the absorbable matrix (as wound packing means 278) may be comprised of collagens or other absorbable materials or combinations of all such materials. U.S. patent application Ser. No. 10/652,100, which was filed by the present inventor with the U.S. Patent and Trademark Office on Aug. 28, 2003, and is hereby incorporated by reference, also discloses various embodiments of an absorbable matrix that may be utilized with various embodiments of the third aspect of the first version of the present invention. It is to be noted, however, that wound packing means 278 may not be utilized in other embodiments of this third aspect of the first version of the invention.

In the embodiment of the third aspect of the first version of the invention illustrated in FIG. 3, the wound treatment device 215 is also comprised of a suction drain 245 and suction drain connection means, which are described in more detail below, to operably connect the reduced pressure supply means 240 to the suction drain 245 so that the suction drain 245 is in fluid communication with the reduced pressure supply means 240 and reduced pressure is supplied to the volume under the flexible overlay 220 in the area of the wound 260 by means of the suction drain 245. In this embodiment, the suction drain 245 is further comprised of a bottom drain portion 245a extending into the area of the wound 260 under the impermeable overlay 220 from a top drain portion 245b positioned within the port 227. In various embodiments, the top drain portion 245b may be permanently or removably attached to the interior surface of the opening 228 of the port 227 using any suitable means, such as an adhesive, or by the top drain portion 245b having a shape adapted so that all or a portion of it fits tightly against all or a portion of the interior surface of the opening 228 in the port 227. It is to be noted that the top drain portion 245b must be sufficiently sealed against the surface of the port 227 in a manner so that reduced pressure can be maintained in the volume under the impermeable overlay 220 in the area of the wound 260. In the embodiment illustrated in FIG. 3, the top drain portion 245b and the bottom drain portion 245a of the suction drain 245 are comprised of polymer tubing that is flexible enough to allow the tubing to easily bend, but rigid enough to prevent the tubing from collapsing during use. In other embodiments, portions of the top drain portion 245b and the bottom drain portion 245a of the suction drain 245 may be comprised of other materials, such as flexible or semi-rigid polymers, plastics, rubber, silicone, or combinations of such materials. In yet other embodiments, the suction drain 245 may have different cross-sectional shapes, such as elliptical, square, rectangular, pentagonal, hexagonal, or other shapes, as long as the suction drain 245 is adapted to provide an approximately hermetic seal with the port 227, as described in more detail above. In still other embodiments, the bottom drain portion 245a of the suction drain 245 may be further comprised of wound suction means that may be used to remove debris, exudate and other matter from the wound 260. In the embodiment illustrated in FIG. 3, the wound suction means is comprised of a distal end portion 245a' of the tubing comprising the bottom drain portion 245a having a plurality of perforations 245a" in the surface of the distal end portion 245a'. In other embodiments, the distal end portion 245a' of the bottom drain portion 245a may have almost any shape or combination of shapes (e.g., circular, elliptical, square, pentagonal, or hexagonal), including a shape different from the remaining portion of the bottom drain portion 245a, may be of almost any size relative to the remaining bottom drain portion 245a (e.g., may be longer or shorter than the remaining bottom drain portion 245a or have a cross-section smaller or larger than the remaining bottom drain portion 245a, or both), may have more or fewer perforations 245a", may have different sizes and shapes of perforations 245a", may extend along different portions of the bottom drain portion 245a, and may be constructed in whole or in part of materials that are not flexible. In embodiments that have a distal end portion 245a', the distal end portion 245a' may be attached to the remaining portion of the bottom drain portion 245a in almost any manner, as long as the remaining bottom drain portion 245a is in fluid communication with the wound suction means 245a'. Examples include an adhesive in some embodiments and a fastening collar in other embodiments. In still other embodiments, the distal end portion 245a' may be fused or welded to the remaining portion of the bottom drain portion 245a. In yet other embodiments, the distal end portion 245a' and the remaining portion of the bottom drain portion 245a may be fabricated as a single piece.

In some embodiments of this first version of the invention, as illustrated in FIG. 3, the top drain portion 245b may extend beyond the top of the port 227 into the area outside the volume of the flexible overlay 220. In some of these embodiments, as is also illustrated in FIG. 3, the suction drain connection means, which may be used to removably connect the reduced pressure supply means 240 to the top drain portion 245b of the suction drain 245 is a variable descending diameter adapter 246 (commonly referred to as a "Christmas tree" adapter) that is placed into the interior volume of the top drain portion 245b at its distal end. In other embodiments, the suction drain connection means may be clamps, fastening collars, or other fasteners or combinations thereof. In yet other embodiments, the top drain portion 245b may be fused or welded to the reduced pressure supply means 240. In still other embodiments, the top drain portion 245b and the portion of the reduced pressure supply means 240 adjacent to the top drain portion 245b may be fabricated as a single piece. In other embodiments, the top drain portion 245b may not extend beyond the top of the port 227 and the reduced pressure supply means 240 may connect directly to the port 227 using any suitable means, such as an adhesive, welding, fusing, clamps, collars or other fasteners, or any combination of such means.

In the embodiment of this third aspect of the first version of the invention illustrated in FIG. 3, the distal end portion 245a' of the suction drain 245 extends into the interior volume of the wound packing means 278. In this embodiment, the wound packing means 278 and the suction drain 245 may be fabricated by snaking the distal end portion 245a' of the suction drain 245 through an internal passageway in the wound packing means 278, such as by pulling the distal end portion 245a' of the suction drain 245 through the passageway using forceps. Alternatively, the wound packing means 278 and the suction drain 245 may be manufactured as a single piece in sterile conditions and then be stored in an aseptic package until ready for use. In other embodiments, the distal end portion 245a' of the suction drain 245 may be placed adjacent or close to the wound packing means 278 in the area of the wound 260. The preferred means of placement of the suction drain 245 relative to the wound packing means 278 is dependent upon the type of wound 260, the wound packing means 278, and the type of treatment desired. Referring to FIG. 3 as an example, it is therefore to be noted that in some embodiments of this third aspect of the first version of the invention, the wound treatment device 215 may utilize a suction drain 245 without utilizing wound packing means 278, while in other embodiments a suction drain 245 may be utilized with wound packing means 278. In addition, in other embodiments of this first version of the invention, the wound treatment device 215 may utilize wound packing means 278 without utilizing a suction drain 245, while in other embodiments wound packing means 278 may be utilized with a suction drain 245.

In the embodiment of the first version of the invention illustrated in FIG. 3, the vacuum system 250, which in conjunction with the wound treatment device 215 also represents a fourth aspect of this first version of the invention, is generally comprised of a suction bulb 281 having an inlet port 282 and an outlet port 283, a bulb connection tubing member 284, an exhaust tubing member 285, an exhaust control valve 286, a filter 287, and a supplemental vacuum system (illustrated schematically and generally designated 250a). In this embodiment, the suction bulb 281 is a hollow sphere that may be used to produce a supply of reduced pressure for use with the wound treatment device 215. In addition, the suction bulb 281 may also be used to receive and store fluid aspirated from the wound 260. The inlet port 282 of the suction bulb 281 is connected to one end of the bulb connection tubing member 284, which is also the reduced pressure supply means 240 in this embodiment. The connection tubing member 284 is connected by suction drain connection means to the top drain portion 245b at its other end in a manner so that the interior volume of the suction bulb 281 is in fluid communication with the suction drain 245. In this embodiment, the bulb connection tubing member 284 is sufficiently flexible to permit movement of the bulb connection tubing member 284, but is sufficiently rigid to resist constriction when reduced pressure is supplied to the suction drain 245 or when the location of the wound 260 is such that the patient must sit or lie upon the bulb connection tubing member 284 or upon the wound treatment device 215. The outlet port 283 of the suction bulb 281 is connected to the exhaust tubing member 285. In this embodiment, the exhaust tubing member 285 is sufficiently flexible to permit movement of the exhaust tubing member 285, but is sufficiently rigid to resist constriction when reduced pressure is supplied to the suction drain 245. The inlet port 282 of the suction bulb 281 may be connected to the bulb connection tubing member 284 and the outlet port 283 of the suction bulb 281 may be connected to the exhaust tubing member 285 using any suitable means, such as by welding, fusing, adhesives, clamps, or any combination of such means. In addition, in some embodiments, which are the preferred embodiments, the suction bulb 281, the bulb connection tubing member 284, and the exhaust tubing member 285 may be fabricated as a single piece. In the illustrated embodiment, the exhaust control valve 286 and the filter 287 are operably connected to the exhaust tubing member 285. In this embodiment, the exhaust control valve 286 is used to regulate the flow of fluids (gases and liquids) to and from the suction bulb 281 and the supplemental vacuum system 250a. In embodiments of the invention that do not have a supplemental vacuum system 250a, the exhaust control valve 286 regulates flow of fluids to and from the suction bulb 281 and the outside atmosphere. Generally, the exhaust control valve 286 allows fluids to flow out of the suction bulb 281 through the outlet port 283, but not to flow in the reverse direction unless permitted by the user of the appliance 210. Any type of flow control valve may be used as the exhaust control valve 286, as long as the valve is capable of operating in the anticipated environment involving reduced pressure and wound 260 exudate. Such valves are well known in the relevant art, such as sprung and unsprung flapper-type valves and disc-type valves. In this embodiment, the filter 287 is operably attached to the exhaust tubing member 285 between the outlet port 283 of the suction bulb 281 and the exhaust control valve 286. The filter 287 prevents potentially pathogenic microbes or aerosols from contaminating the exhaust control valve 286 (and supplemental vacuum system 250a), and then being vented to atmosphere. The filter 287 may be any suitable type of filter, such as a micropore filter. In other embodiments, the filter 287 may also be a hydrophobic filter that prevents any exudate from the wound 260 from contaminating the exhaust control valve 286 (and the supplemental vacuum system 250a) and then being vented to atmosphere. In still other embodiments, the filter 287 may perform both functions. It is to be noted, however, that the outlet port 283, the exhaust control valve 286, the filter 287, or any combination of the exhaust control valve 286 and the filter 287, need not be utilized in connection with the vacuum system 250 in other embodiments of the invention.

In some embodiments of these third and forth aspects of the first version of the invention illustrated in FIG. 3 that do not utilize a supplemental vacuum system 250a, the suction bulb 281 may be used to produce a supply of reduced pressure in the following manner. First, the user of the appliance 210 appropriately seals all of the component parts of the appliance 210 in the manner described herein. For example, the impermeable overlay 220 is sealed (or placed adjacent) to the body 170 and the suction drain 245 is sealed to the bulb connection tubing member 284 and the surface of the port 227. The user then opens the exhaust control valve 286 and applies force to the outside surface of the suction bulb 281, deforming it in a manner that causes its interior volume to be reduced. When the suction bulb 281 is deformed, the gas in the interior volume is expelled to atmosphere through the outlet port 283, the exhaust tubing member 285, the filter 287, and the exhaust control valve 286. The user then closes the exhaust control valve 286 and releases the force on the suction bulb 286. The suction bulb 281 then expands, drawing fluid from the area of the wound 260 under the wound treatment device 215 into the suction bulb 281 through the suction drain 245 and causing the pressure in such area to decrease. To release the reduced pressure, the user of the appliance 210 may open the exhaust control valve 286, allowing atmospheric air into the interior volume of the suction bulb 281. The level of reduced pressure may also be regulated by momentarily opening the exhaust control valve 286.

The suction bulb 281 may be constructed of almost any fluid impermeable flexible or semi-rigid material that is suitable for medical use and that can be readily deformed by application of pressure to the outside surface of the suction bulb 281 by users of the appliance 210 and still return to its original shape upon release of the pressure. For example, the suction bulb 281 may be constructed of rubber, neoprene, silicone, or other flexible or semi-rigid polymers, or any combination of all such materials. In addition, the suction bulb 281 may be of almost any shape, such as cubical, ellipsoidal, or polygonal. The suction bulb 281 may also be of varying size depending upon the anticipated use of the suction bulb 281, the size of the wound treatment device 215, use of a supplemental vacuum system 250a, the level of reduced pressure desired, and the preference of the user of the appliance 210. In the embodiment of the invention illustrated in FIG. 3, the supplemental vacuum system 250a is connected to the exhaust tubing member 285 and is used to provide a supplemental supply of reduced pressure to the suction bulb 281 and wound treatment device 215. In this embodiment, the supplemental vacuum system 250a may have substantially the same structure, features, characteristics and operation of the various embodiments of the vacuum system 50 of the first version of the invention described above and illustrated in connection with FIG. 2A and FIG. 2B. It is to be noted, however, that the supplemental vacuum system 250a need not be used in connection with the vacuum system 280 in other embodiments of the invention.

Except as described below, the wound treatment appliance 210 described above and illustrated in connection with FIG. 3 may generally be used in a manner similar to the wound treatment appliance 110 described above and illustrated in connection with FIG. 2A and FIG. 2B. As a result, except as described below, the example of how the embodiment of the wound treatment appliance 110 and the flexible overlay 120 described above and illustrated in connection FIG. 2A may be used in treatment of a wound 160 also applies to the embodiment of the appliance 210 of the third aspect of the first version of the invention described above and illustrated in connection with FIG. 3. In the case of the embodiment illustrated in FIG. 3, however, the wound packing means 278 is placed into the wound 260 prior to placement of the flexible overlay 220 over the portion of the wound 260 to be treated. In addition, the flexible overlay 220 is placed over the wound packing means 278. In embodiments where the distal end portion 245a" of a suction drain 245 is placed into the interior volume of, or adjacent to, the wound packing means 278, the distal end portion 245a' of the suction drain 245 is also placed in the appropriate position before the flexible overlay 220 is placed over the wound 260. In embodiments utilizing a suction drain 245 without wound packing means 278, the suction drain 245 is installed in the flexible overlay 220 before the flexible overlay 220 is placed over the wound 260.

Another embodiment of the first version of the invention is the wound treatment appliance 310 illustrated in FIG. 4. FIG. 4 also illustrates another example of how the embodiment of the flexible overlay 20 described above and illustrated in connection with FIG. 1A may be used to provide reduced pressure treatment for a wound 360 on the body 370 of a patient. In this embodiment, the wound treatment appliance 310 is comprised of a flexible overlay 320 and a vacuum system, generally designated 350, that is operably connected to, and provides a supply of reduced pressure to, the flexible overlay 320. In addition, in this embodiment, the vacuum system 350 is further comprised of a reduced pressure supply source, generally designated 330, which is described in more detail below, and reduced pressure supply means, generally designated 340, which are described in more detail below. In this embodiment, the reduced pressure supply means 340 are used to connect the reduced pressure supply source 330 to the flexible overlay 320 in a manner so that reduced pressure is supplied to the area under the flexible overlay 320, as described in more detail below. In the embodiment of the first version of the invention illustrated in FIG. 4, the flexible overlay 320 has substantially the same structure, features and characteristics as the flexible overlay 20 described above and illustrated in connection with FIG. 1A. It is to be noted, however, that in other embodiments of this first version of the invention, the flexible overlay 320 may have substantially the same structure, features and characteristics as any embodiment of all of the flexible overlays 20, 20a, 20b of the first version of the invention described above and illustrated in connection with FIG. 1A, FIG. 1B, and FIG. 1C, respectively. In this example, the flexible overlay 320 is placed over and encloses the entire wound 360, which is at the distal end of an amputated limb. It is to be noted that in other embodiments, the appliance 310 may also be comprised of tissue protection means 375, which may be substantially the same as the tissue protection means 175 of the first version of the invention described above and illustrated in connection with FIG. 2A. In other embodiments, the appliance 310 may also be comprised of wound packing means (not illustrated), which may be substantially the same as the wound packing means 278 of the first version of the invention described above and illustrated in connection with FIG. 3.

In the embodiment of the first version of the invention illustrated in FIG. 4, the reduced pressure supply source 330 of the vacuum system 350, which produces a source of reduced pressure or suction that is supplied to the flexible overlay 320, includes a small, portable vacuum pump 331, a filter 333, and a power source (not illustrated) that is contained within the housing for the portable vacuum pump 331. In the illustrated embodiment, predetermined amounts of suction or reduced pressure are produced by the portable vacuum pump 331. The portable vacuum pump 331 is preferably controlled by a control device (not illustrated) that is also located within the housing for the portable vacuum pump 331, which may provide substantially the same functions as the control device 132 of the first version of the invention described above and illustrated in connection with FIG. 2A and FIG. 2B. Except for its smaller size, the portable vacuum pump 331 may operate in substantially the same manner as the vacuum pump 131 of the first version of the invention described above and illustrated in connection with FIG. 2A and FIG. 2B. In the embodiment illustrated in FIG. 4, the filter 333 may have the same structure, features, characteristics and operation, and provide substantially the same functions, as the filter 133 of the first version of the invention described above and illustrated in connection with FIG. 2A and FIG. 2B. The power source may be any source of energy currently known in the art or that may be developed in the art in the future that may be used to power the portable vacuum pump 331. For example, in some embodiments, the power source may be a fuel cell or battery. In the illustrated embodiment, the filter 333 is rigidly connected to the portable vacuum pump 331. It is to be noted that in other embodiments of the first version of the invention, the reduced pressure supply source 330 may not have a filter 333.

In the embodiment of the first version of the invention illustrated in FIG. 4, the reduced pressure supply means 340 of the vacuum system 350, which is used to connect the reduced pressure supply source 330 to a port 327 on the flexible overlay 320 so that reduced pressure is supplied to the area of the wound 360 under the flexible overlay 320, is comprised of at least one 25 tubing member 341. In this embodiment, the at least one tubing member 341 is a rigid tubing member. In other embodiments, the at least one tubing member 341 may be sufficiently flexible to permit movement of the at least one tubing member 341, but is sufficiently rigid to resist constriction when reduced pressure is supplied to the port 327 or when the location of the wound 360 is such that the patient must sit or lie upon the at least one tubing member 341 or upon the flexible overlay 320. In the embodiment illustrated in FIG. 4, the at least one tubing member 341 is connected to the port 327 by inserting one end of the at least one tubing member 341 into an opening 328 in the port 484 and sealing (such as with an adhesive) the at least one tubing member 341 to the port 327. It is to be noted that in other embodiments, the at least one tubing member 341 may be connected to the port 327 using any suitable means currently known in the relevant art or developed in the relevant art in the future. Examples include the suction drain connection means of the first version of the invention discussed above and illustrated in connection with FIG. 3. Similar means may be used to connect the other end of the at least one tubing member 341 to the reduced pressure supply source 330 providing the reduced pressure. In other embodiments of this first version of the invention, the reduced pressure supply means 340 may further comprise a fluid collection system (not illustrated), which may generally have the same structure, features, characteristics and operation, and perform the same functions, as the fluid collection system 142 of the first version of the invention described above and illustrated in connection with FIG. 2A and FIG. 2B.

An embodiment of a second version of the invention is the wound treatment appliance 410 illustrated in FIG. 5. In this embodiment, the appliance 410 is comprised of a wound treatment device 415, which is further comprised of an impermeable overlay 420, a collection chamber 490 to receive and hold fluid aspirated from the wound 460, collection chamber attachment means to operably attach the collection chamber 490 to the overlay 420, as described in more detail below, and reduced pressure supply means, generally designated 440, which are described in more detail below. In this embodiment, the impermeable overlay 420 is adapted to be placed over and enclose all or a portion of the wound 460 in the same manner as the flexible overlay 20 described in detail above and illustrated in connection with FIG. 1A. It is to be noted, however, that the impermeable overlay 420 illustrated in FIG. 5 is shown in position on the body 470 over the wound 460, but not in its collapsed state. In the illustrated embodiment, and except as described in more detail below, the impermeable overlay 420 has substantially the same structure, features and characteristics as the flexible overlay 20 described in detail above and illustrated in connection with FIG. 1A. In the various embodiments of this second version of the invention, except as described in more detail below, the impermeable overlay 420 may have substantially the same structure, features, characteristics and operation as the embodiments of the flexible overlays 20, 20a, 20b, 120, 220 described in more detail above and illustrated in connection with FIG. 1A, FIG. 1B, FIG. 1C, FIG. 2A, and FIG. 3, respectively. In addition, the impermeable overlay 420 may be almost any type of semi-rigid or rigid wound covering apparatus currently known in the relevant art or that may be developed in the relevant art in the future that has a port and is designed to cover and enclose a wound and maintain reduced pressure in the area of the wound under the wound covering apparatus. For example, the impermeable overlay 420 may generally have substantially the same structure, features and characteristics as the embodiments of the rigid or semi-rigid generally conically-shaped or cup-shaped wound covers described in U.S. patent application Ser. No. 10/652,100, which was filed by the present inventor with the U.S. Patent and Trademark Office on Aug. 28, 2003, and U.S. patent application entitled "Improved Reduced Pressure Wound Treatment Appliance," which was filed by the present inventor with the U.S. Patent and Trademark Office on or about Dec. 30, 2004, the disclosures of which are incorporated herein by reference. In the illustrated embodiment, reduced pressure supply means, generally designated 440, which are described in more detail below, are used to operably connect the collection chamber 490 to a reduced pressure supply source, generally designated 430, which is described in more detail below, that provides a supply of reduced pressure to the collection chamber 490, so that the volume within the collection chamber 490 and under the impermeable overlay 420 in the area of the wound 460 to be treated are supplied with reduced pressure by the reduced pressure supply source 430. Together, the reduced pressure supply means 440 and the reduced pressure supply source 430 comprise a vacuum system, generally designated 450. In the various embodiments of this second version of the invention, except as described in more detail below, the reduced pressure supply means 440 used to connect the reduced pressure supply source 430 to the collection chamber 490 may have substantially the same structure, features, characteristics and operation as the reduced pressure supply means 140, 240, 340 described above and illustrated in connection with FIG. 2A, FIG. 2B, FIG. 3, and FIG. 4, respectively. In addition, in the various embodiments of this second version of the invention, except as described in more detail below, the reduced pressure supply source 430 used to provide the supply of reduced pressure to the collection chamber 490 may have substantially the same structure, features, characteristics and operation as the reduced pressure supply source 130, 280, 330 described above and illustrated in connection with FIG. 2A, FIG. 2B, FIG. 3, and FIG. 4, respectively.

In the embodiment of the appliance 410 illustrated in FIG. 5, the collection chamber 490 is approximately cylindrical in shape. In other embodiments, the collection chamber 490 may have other shapes. For example, the collection chamber may be shaped approximately as a sphere, ellipsoid, cube, polyhedron, or other shape or combination of such shapes, as long as the collection chamber 490 has an interior volume to receive and hold fluid aspirated from the wound 460. The collection chamber 490 may also be of almost any size. For example, the collection chamber 490 may be relatively small where the wound 460 is expected to aspirate only a small volume of fluid. On the other hand, the collection chamber 490 may be relatively large where it is expected that the wound 460 will aspirate a large volume of fluid. As a result, the preferred size of the collection chamber 490 is dependent upon the size of the wound 460 to be treated, the size of the impermeable overlay 420, the type of wound 460 to be treated, and the preference of the user of the appliance 410. In the various embodiments of this second version of the invention, the collection chamber 490 may be comprised of almost any medical grade material that is currently known in the art or that may be developed in the art in the future, as long as such material is fluid-impermeable and suitable for purposes of wound treatment (e.g., can be sterilized and does not absorb significant amounts of wound 460 exudate). For example, the collection chamber 490 may be comprised of rubber (including neoprene) and polymer materials, such as silicone, silicone blends, silicon substitutes, polyvinyl chloride, polycarbonates, polyester-polycarbonate blends, or a similar polymer, or combinations of all such materials. It is to be noted that the collection chamber 490 may have a rigid or semi-rigid structure in some embodiments. In other embodiments, the collection chamber 490 may be more flexible so that it can be squeezed in a manner similar to the suction bulb 281, as described above and illustrated in connection with FIG. 3. Although the collection chamber 490 may be constructed of a material different from the material comprising the impermeable overlay 420 in various embodiments of the invention, the collection chamber 490 is preferably constructed from the same material comprising the impermeable overlay 420. The collection chamber 490 may be constructed using any suitable means currently known in the art or that may be developed in the art in the future. For example, a collection chamber 490 constructed of silicone may be manufactured by means of injection molding.

In the various embodiments of this second version of the invention, the collection chamber attachment means operably attaches the collection chamber 490 to the impermeable overlay 420 in a manner so that exudate and reduced pressure are permitted to flow between the collection chamber 490 and the volume under the impermeable overlay 420 in the area of the wound 460. Also, in the various embodiments of the second version of the invention, as illustrated by the appliance 410 in FIG. 5, the collection chamber 490 is positioned approximately adjacent to the impermeable overlay 420 on the side of the impermeable overlay 420 opposite the wound 460. Although the collection chamber 490 and the collection chamber attachment means are positioned approximately at the apex of the impermeable overlay 420 in the illustrated embodiment, in other embodiments the collection chamber 490 and collection chamber attachment means may be positioned at almost any location on the surface of the impermeable overlay 420 opposite the wound 460, as long as the collection chamber 490 and collection chamber attachment means do not materially interfere with the operation of the impermeable overlay 420. As illustrated in FIG. 5, the collection chamber attachment means may be a rigid or semi-rigid connecting member 491 between the collection chamber 490 and the impermeable overlay 420. In this embodiment, the connecting member 491 is approximately cylindrical in shape and has a port 492 therein, which is also approximately cylindrical in shape and extends between the collection chamber 490 and the impermeable overlay 420 so that fluids can flow between the collection chamber 490 and the impermeable overlay 420. In other embodiments, the connecting member 491 and the port 492 may be of almost any shape or combination of shapes. For example, the connecting member 491 and the port 492 may be shaped approximately as a sphere, ellipsoid, cube, polygon, paraboloid, or any other shape or combination of shapes, as long as the connecting member 491 provides a rigid or semi-rigid connection between the collection chamber 490 and the impermeable overlay 420 that is adequate to support the collection chamber 490 when it is filled with exudate from the wound 460, and the port 492 is of a size and shape adequate to allow the flow of exudate from the wound 460 between the collection chamber 490 and the impermeable overlay 420. For example, the collection chamber 490 in some embodiments may have approximately the same outside diameter as the connecting member 491, as illustrated by the phantom lines 493 in FIG. 5. The connecting member 491 may generally be constructed of any material that is suitable for construction of the collection chamber 490 or the impermeable overlay 420, and is preferably constructed from the same materials as the collection chamber 490 and the impermeable overlay 420. In various embodiments, the collection chamber 490 and the impermeable overlay 420 may be connected to the connecting member 491 using any suitable means, such as by adhesives, welding, fusing, clamps, and other fastening means or combinations of such means. In yet other embodiments, the collection chamber 490, the impermeable overlay 420, and the connecting member 491 may be fabricated as a single piece. In still other embodiments, one or more of the connections between the collection chamber 490, the impermeable overlay 420, and the connecting member 491 may provide for removing one component from another to empty fluid from the collection chamber 490. For example, the collection chamber 490, the impermeable overlay 420, and the connecting member 491 may each be threaded at their points of connection so that they can be screwed together and then unscrewed when desired. In still other embodiments, the collection chamber 490 and the impermeable overlay 420 may be directly connected together without a connecting member 491, as long as the connection allows fluid to flow between the collection chamber 490 and the impermeable overlay 420. Such connection may be made using any of the means described above in this paragraph.

In some embodiments of this second version of the invention, as illustrated in FIG. 5, the connecting member 491, as the collection chamber attachment means, may be further comprised of a flow control means, which is described in more detail below, operably positioned between the collection chamber 490 and the impermeable overlay 420. In these embodiments, the flow control means permits fluid aspirated from the wound 460 to flow from the volume under the impermeable overlay 420 in the area of the wound 460 through the port 492 into the collection chamber 490, but not in the opposite direction. In the illustrated embodiment, the flow control means is comprised of a flapper-type valve 494. In this embodiment, the valve 494 has two flapper members 494*a* that are hinged at their distal end to a portion of the connecting member 491, and the flapper members 494*a* are of a shape and size adapted to substantially close the port 492 when they are positioned in the closed position. In other embodiments, the flow control means may be comprised of a disc-type valve, wherein the disc of the valve moves with the flow of fluids and contacts a seat disposed around the perimeter of the port when the flow of fluids is misdirected, so that the port is sealed closed and prevents fluid flow in the wrong direction. In some embodiments, as illustrated in FIG. 5, the collection chamber 490 may be further comprised of a shroud 495 (illustrated by the phantom lines) that extends from a portion of the collection chamber 490 to the impermeable shield 420. In these embodiments, the shroud 495 is approximately tubular in shape. In other embodiments, the shroud 495 may have other shapes. The shroud 495 generally provides additional support for the collection chamber 490 and may also provide for a more aesthetically pleasing appearance for the appliance 410. In addition, in the embodiment of the appliance 410 illustrated in FIG. 5, the reduced pressure supply means 440 is connected to the collection chamber 490 by means of a stopper 445 adapted to fit into an opening 496 in the collection chamber 490. The stopper 445 forms a seal with the portion of the collection chamber 490 adjacent to the opening 496 so that reduced pressure can be maintained within the interior volume of the collection chamber 490. In this embodiment, the reduced pressure supply means is comprised of a tubular member 441 that is positioned in a port 446 in the stopper 445 at one end and is connected to the reduced pressure supply source 430 at the other end.

The embodiment of the appliance 410 illustrated in FIG. 5 may be used to treat a wound 460 on a body 470 using a method comprising the following steps. First, the wound treatment device 415 is positioned on the body 470 over the area of the wound 460 to be treated. Next, the vacuum system 450 is operably connected to the collection chamber 490. The impermeable overlay 420 may then be collapsed in the approximate direction of the wound 460 when reduced pressure is supplied to the volume under the impermeable overlay 420 in the area of the wound 460 so that an approximately hermetic seal (as illustrated and described in more detail above in connection with FIG. 2A) is formed between the impermeable overlay 420 and the body 470 in the area of the wound 460. Next, reduced pressure is maintained in the volume of the impermeable overlay 420 in the area of the wound 460 until the area of the wound 460 being treated has progressed toward a selected stage of healing. In other embodiments, the method may further comprise the step of placing tissue protection means 475, which may be substantially the same as the tissue protection means 175, as described above and illustrated in connection with FIG. 2A, on the tissue 471 of the body 470 that is to be approximately adjacent to the impermeable overlay 420, such step being performed prior to positioning the impermeable overlay 420 over the area of the wound 460 to be treated. In yet other embodiments, the method further comprises the step of placing wound packing means (not illustrated), which may be substantially the same as the wound packing means 278, as described above and illustrated in connection with FIG. 3, between the wound 460 and the impermeable overlay 420 in the area of the wound 460 to be treated, such step being performed prior to positioning the impermeable overlay 420 over the area of the wound 460 to be treated. In still other embodiments, the reduced pressure under the impermeable overlay 420 in the area of the wound 460 is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure. In yet other embodiments, the method is further comprised of the step of emptying any fluid collected in the collection chamber 490. This step may be performed after the impermeable overlay 420 is collapsed in the approximate direction of the wound 460 and may also be performed before or after the area of the wound 460 being treated has progressed toward a selected stage of healing.

Figure 6:
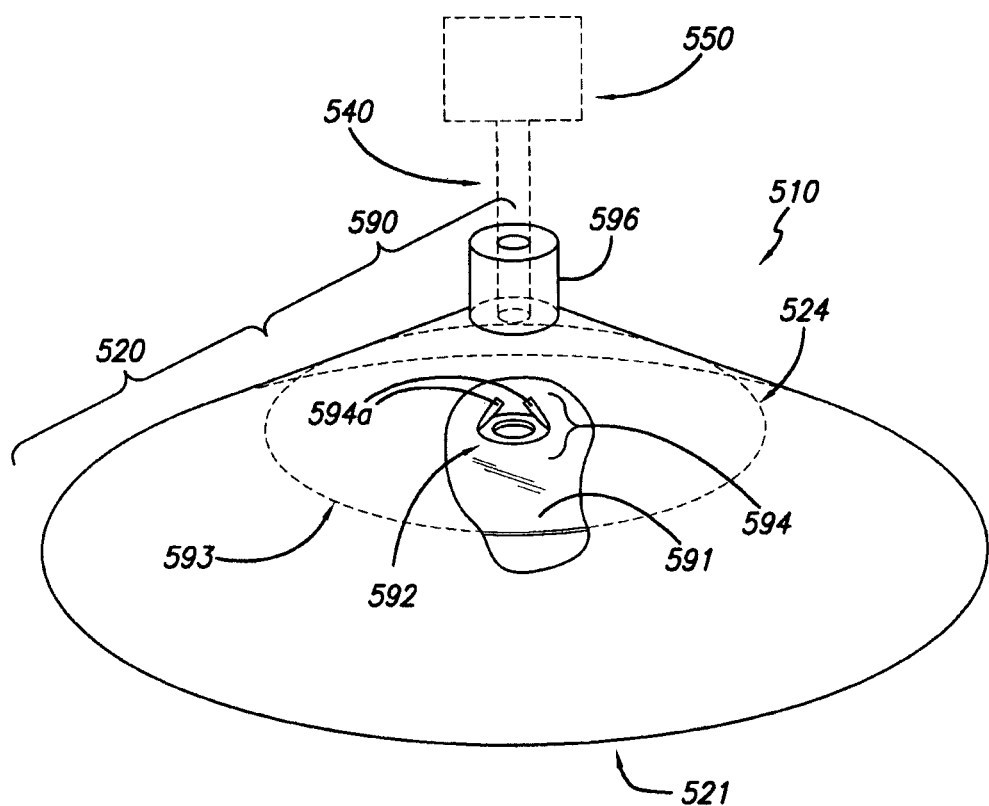
FIG. 6 is a view of another embodiment of a wound treatment appliance of a second version of the present invention, in which an embodiment of an impermeable flexible overlay is shown in partially broken away perspective view from the side of and above the flexible overlay (as the flexible overlay would be oriented when placed on the body of a patient), and in which an embodiment of a vacuum system, depicted generally and shown in schematic elevation view, provides reduced pressure within the area under the flexible overlay.

Another embodiment of the second version of the invention is the wound treatment appliance 510 illustrated in FIG. 6. In this embodiment, the appliance 510 is comprised of an impermeable overlay 520, a collection chamber 590 to receive and hold fluid aspirated from a wound (not shown), collection chamber attachment means to operably attach the collection chamber 590 to the overlay 520, as described in more detail below, and reduced pressure supply means, generally designated 540, which are described in more detail below. In this embodiment, the impermeable overlay 520 is adapted to be placed over and enclose all or a portion of a wound in the same manner as the flexible overlay 20a described in detail above and illustrated in connection with FIG. 1B. It is to be noted that the impermeable overlay 520 illustrated in FIG. 6 is not shown in its collapsed state. In the illustrated embodiment, and except as described in more detail below, the impermeable overlay 520 has substantially the same structure, features and characteristics as the flexible overlay 20a described in detail above and illustrated in connection with FIG. 1B. In other embodiments, the impermeable overlay 520 may be of other shapes and have other features. For example, the impermeable overlay 520 may be of the shape and have the features illustrated and described above in connection with the appliance 10b of FIG. 1C. In the embodiment illustrated in FIG. 6, the reduced pressure supply means 540, which are described in more detail below, may be used to operably connect the collection chamber 590 to a reduced pressure supply source (not shown), which is described in more detail below, that provides a supply of reduced pressure to the collection chamber 590, so that the volume within the collection chamber 590 and under the impermeable overlay 520 in the area of the wound to be treated are supplied with reduced pressure by the reduced pressure supply source. Together, the reduced pressure supply means 540 and the reduced pressure supply source comprise a vacuum system, generally designated 550. In this embodiment of the second version of the invention, except as described in more detail below, the reduced pressure supply means 540 used to connect the reduced pressure supply source to the collection chamber 590 may have substantially the same structure, features, characteristics and operation as the reduced pressure supply means 140, 240, 340 described above and illustrated in connection with FIG. 2A, FIG. 2B, FIG. 3, and FIG. 4, respectively. In addition, in this embodiment of the second version of the invention, except as described in more detail below, the reduced pressure supply source used to provide the supply of reduced pressure to the collection chamber 590 may have substantially the same structure, features, characteristics and operation as the reduced pressure supply source 130, 280, 330 described above and illustrated in connection with FIG. 2A, FIG. 2B, FIG. 3, and FIG. 4, respectively. The embodiment of the appliance 510 illustrated in FIG. 6 may be used to treat a wound on a body using substantially the same method described above in connection with the appliance 410 illustrated in FIG. 5.

In the embodiment illustrated in FIG. 6, the collection chamber 590 is positioned approximately adjacent to the impermeable flexible overlay 520 on the side of the impermeable flexible overlay 520 opposite the wound. In this embodiment, the collection chamber attachment means, as described in more detail below, is comprised of a membrane 591. In this embodiment, the membrane 591 acts as a barrier separating the collection chamber 590 and the impermeable flexible overlay 520, so that the membrane 591 acts as a portion of the surface of the collection chamber 590 and a portion of the surface of the impermeable flexible overlay 520. In addition, the membrane 591 has at least one port 592 therein so that the volume within the collection chamber 590 is in fluid communication with the volume under the impermeable flexible overlay 520 in the area of the wound. It is to be noted that there may be more than one port 592 in other embodiments. The number of ports 492 is generally dependent upon the size and shape of the collection chamber 590, the size and shape of the impermeable flexible overlay 520, the anticipated amount of exudate to be aspirated from the wound, the level of reduced pressure to be utilized, and the individual preference of the user of the appliance 510. In embodiments where the impermeable flexible overlay 520 has an approximately elongated conical shape, as illustrated in FIG. 6, the impermeable flexible overlay 520 may have a base end opening 521 and a top end opening 524 opposite the base end opening 521. In these embodiments, the base end opening 521 may have an either approximately circular shape or approximately elliptical shape sized to be placed over and enclose the area of the wound to be treated. The top end opening 524 may have either an approximately circular shape or approximately elliptical shape. In the illustrated embodiments, the membrane 591 is adapted to be of the same shape and size as the top end opening 524 and the membrane 591 is positioned so that it is attached to the entire perimeter of the top end opening 524 and covers the entire top end opening 524. The membrane 591 may be attached to the perimeter of the top end opening 524 by any suitable means currently known in the relevant art or developed in the art in the future. Examples of such means include welding or fusing the membrane 591 to the perimeter of the top end opening 524. Alternatively, the membrane 591 may be fabricated as a single piece with the impermeable flexible overlay 520.

In the embodiment of the appliance 510 illustrated in FIG. 6, the collection chamber 590 has an approximately elongated conical shape, a chamber bottom end opening 593, and a reduced pressure supply port 596 positioned at the apex of the collection chamber 590 opposite the chamber bottom end opening 593. The reduced pressure supply port 596 may be used to operably connect the reduced pressure supply means 540 to the collection chamber 590. In some embodiments, a micropore or hydrophobic filter or both (not shown) may be operably positioned within the reduced pressure supply port 596 or the connection with the reduced pressure supply means 540 to retain the exudate from the wound within the collection container 590 or to prevent exudate from contaminating portions of the vacuum system 550, or both. In the illustrated embodiment, the chamber bottom end opening 593 is adapted to be of approximately the same size and shape as the top end opening 524 of the impermeable flexible overlay 520. In other embodiments, the collection chamber 590 may be of other shapes and sizes and its bottom end opening 593 may not necessarily be of the same size and shape as the top end opening 524 of the impermeable flexible overlay 520. In all embodiments, however, the collection chamber 590 is attached to the membrane 591 in a manner so that the membrane 591 acts as a portion of the surface of the collection chamber 590 and so that the volume within the collection chamber 590 is airtight, except for the at least one port 592 and the reduced pressure supply port 596. In the preferred embodiment, the collection chamber 590 and the impermeable flexible overlay 520 have the shapes illustrated in FIG. 6. The membrane 591 may be attached to the perimeter of the chamber bottom end opening 593 by any suitable means currently known in the relevant art or developed in the art in the future. Examples of such means include welding or fusing the membrane 591 to the perimeter of the chamber bottom end opening 593. Alternatively, the membrane 591 or the impermeable flexible overlay 520, or both, may be fabricated as a single piece with the collection chamber 590. The preferred shapes and sizes of the collection chamber 590 and the impermeable flexible overlay 520 are dependent upon the size and type of wound to be treated, the area of the body on which the wound is positioned, the level of reduced pressure to be utilized, the amount of collapse of the impermeable flexible overlay 520 desired, and the preference of the user of the appliance 510. In this embodiment of the second version of the invention, the collection chamber 590 may be comprised of almost any medical grade material that is currently known in the art or that may be developed in the art in the future, as long as such material is fluid-impermeable and suitable for purposes of wound treatment (e.g., can be sterilized and does not absorb significant amounts of wound exudate). For example, the collection chamber 590 may be comprised of rubber (including neoprene) and flexible polymer materials, such as silicone, silicone blends, silicone substitutes, polyvinyl chloride, polycarbonates, polyester-polycarbonate blends, or a similar polymer, or combinations of all such materials. It is to be noted that the collection chamber 590 may have a rigid or semi-rigid structure in some embodiments. In other embodiments, the collection chamber 590 may be more flexible so that it can be squeezed in a manner similar to the suction bulb 281, as described above and illustrated in connection with FIG. 3. Although the collection chamber 590 may be constructed of a material different from the material comprising the impermeable overlay 520 in various embodiments of the invention, the collection chamber 590 is preferably constructed from the same material comprising the impermeable overlay 520. The collection chamber 590 may be constructed using any suitable means currently known in the art or that may be developed in the art in the future. For example, a collection chamber 590 constructed of silicone may be manufactured by means of injection molding.

In the embodiment of the second version of the invention illustrated in FIG. 6, the membrane 591 and its means of being sealed to the perimeters of the top end opening 524 and the chamber bottom end opening 593, together as collection chamber attachment means, operably attach the collection chamber 590 to the impermeable overlay 520 in a manner so that exudate and reduced pressure are permitted to flow between the collection chamber 590 and the volume under the impermeable overlay 520 in the area of the wound. In the embodiment illustrated in FIG. 6, the at least one port 592 is approximately cylindrical in shape and extends between the collection chamber 590 and the impermeable overlay 520 so that fluids can flow between the collection chamber 590 and the impermeable overlay 520. In other embodiments, the at least one port 592 may be of almost any shape or combination of shapes. In some embodiments of this second version of the invention, as illustrated in FIG. 6, the membrane 591 comprising the collection chamber attachment means may be further comprised of a flow control means, which is described in more detail below, operably connected with the at least one port 592 and positioned between the collection chamber 590 and the impermeable overlay 520. In these embodiments, the flow control means permits fluid aspirated from the wound to flow from the volume under the impermeable overlay 520 in the area of the wound 560 through the at least one port 592 into the collection chamber 590, but not in the opposite direction. In the illustrated embodiment, the flow control means is comprised of a flapper-type valve 594. In this embodiment, the valve 594 has two flapper members 594a that are hinged at their distal end to a portion of the membrane 491 or supporting structure surrounding the at least one port 492 and the flapper members 594a are of a shape and size adapted to substantially close the at least one port 592 when they are positioned in the closed position. In other embodiments, the flow control means may be comprised of a disc-type of valve.

What is claimed is:

1. An apparatus for administering reduced pressure treatment to a wound on a body, comprising:
    a wound cover positionable over the wound and adapted to maintain reduced pressure under the wound cover, the wound cover having an elliptically-shaped perimeter;
    a membrane attached to a lower surface of the wound cover, the membrane having an elliptically-shaped perimeter smaller in dimension than the elliptically-shaped perimeter of the wound cover;
    a chamber defined between the wound cover and the membrane;
    an opening in the wound cover above the chamber; and
    tubing connected to the opening and configured to provide reduced pressure to the chamber;
    wherein a portion of the wound cover beyond the elliptically-shaped perimeter of the membrane is configured to be sealed to skin surrounding the wound.

2. The apparatus of claim 1, wherein the apparatus is configured to be applied over at least a portion of the wound and removed from the wound as a single integral unit.

3. The apparatus of claim 1, wherein the wound cover further comprises an adhesive applied to the lower surface of the wound cover beyond the perimeter of the membrane.

4. The apparatus of claim 1, wherein said tubing passes through the opening into the chamber.

5. The apparatus of claim 1, further comprising a drain configured to be attached to, and configured to be in fluid communication with, the tubing, wherein the drain is positioned inside the chamber.

6. The apparatus of claim 5, wherein the drain is configured to resist constriction upon the administering of reduced pressure to the chamber.

7. The apparatus of claim 5, wherein the drain comprises an elliptical shape.

8. The apparatus of claim 5, wherein the drain further comprises a distal portion configured to be in fluid communication with the tubing, the distal portion attached to a lower surface of the drain, wherein the distal portion comprises a plurality of holes.

9. The apparatus of claim 1, wherein the membrane comprises a barrier between the chamber and the wound cover so that the membrane acts as a portion of a surface of the chamber and a portion of a surface of the wound cover.

10. The apparatus of claim 9, wherein the membrane further comprises at least one port therein so that the chamber is in fluid communication with the wound.

11. The apparatus of claim 1, wherein the membrane is welded or fused to a lower surface of the wound cover.

12. The apparatus of claim 1, wherein the membrane is fabricated as a single piece with the wound cover.

13. The apparatus of claim 1, further comprising a reduced pressure supply source in fluid communication with the tubing and configured to supply reduced pressure to the chamber.

14. The apparatus of claim 13, wherein the reduced pressure supply source comprises a vacuum pump.

15. The apparatus of claim 14, wherein the vacuum pump is a portable vacuum pump.

\* \* \* \* \*